US011573240B2

(12) United States Patent
Ivanova et al.

(10) Patent No.: US 11,573,240 B2
(45) Date of Patent: Feb. 7, 2023

(54) USE OF RECEPTOR-BINDING DOMAIN DERIVED FROM BOVINE LEUKEMIA VIRUS FOR THE DIAGNOSIS OR TREATMENT OF CATIONIC L-AMINO ACID TRANSPORTER-RELATED DISEASES

(71) Applicants: METAFORA BIOSYSTEMS, Évry (FR); CENTRE NATIONAL DE LA RECHERCHE SCIENTIFIQUE, Paris (FR); UNIVERSITÉ DE MONTPELLIER, Montpellier (FR); UNIVERSITÉ PARIS CITÉ, Paris (FR)

(72) Inventors: Svilena Ivanova, Montpellier (FR); Donatella Giovannini, Montpellier (FR); Julien Bellis, Montpellier (FR); Jawida Lezaar, Montpellier (FR); Vincent Petit, Paris (FR); Jean-Luc Battini, Montpellier (FR); Marc Sitbon, Montpellier (FR); Valérie Courgnaud, Montpellier (FR)

(73) Assignees: METAFORA BIOSYSTEMS, Évry (FR); CENTRE NATIONAL DE LA RECHERCHE SCIENTIFIQUE, Paris (FR); UNIVERSITÉ DE MONTPELLIER, Montpellier (FR); UNIVERSITÉ PARIS CITÉ, Paris (FR)

( * ) Notice: Subject to any disclaimer, the term of this patent is extended or adjusted under 35 U.S.C. 154(b) by 0 days.

(21) Appl. No.: 15/777,087

(22) PCT Filed: Nov. 18, 2016

(86) PCT No.: PCT/EP2016/078163

§ 371 (c)(1),
(2) Date: May 17, 2018

(87) PCT Pub. No.: WO2017/085271

PCT Pub. Date: May 26, 2017

(65) Prior Publication Data

US 2018/0335435 A1 Nov. 22, 2018

(30) Foreign Application Priority Data

Nov. 18, 2015 (EP) .................................... 15195252

(51) Int. Cl.
*G01N 33/68* (2006.01)
*A61K 38/00* (2006.01)

(52) U.S. Cl.
CPC .......... *G01N 33/6872* (2013.01); *A61K 38/00* (2013.01); *G01N 2800/26* (2013.01)

(58) Field of Classification Search
CPC ........... A61K 2100/00; A61K 2123/00; A61K 38/00; G01N 33/6872; G01N 2800/26
USPC .......... 424/1.11, 1.49, 1.65, 1.69, 1.73, 1.81, 424/1.85, 1.89, 9.1, 9.2
See application file for complete search history.

(56) References Cited

U.S. PATENT DOCUMENTS

| | | | | |
|---|---|---|---|---|
| 9,791,435 B2 * | 10/2017 | Sitbon | .................. | G01N 33/537 |
| 2013/0203080 A1 * | 8/2013 | Sitbon | .................. | G01N 33/537 435/7.23 |

FOREIGN PATENT DOCUMENTS

| | | |
|---|---|---|
| EP | 0284492 | 9/1988 |
| JP | 2013-539856 A | 10/2013 |
| WO | 2012/035166 | 3/2012 |
| WO | 2012/035369 A1 | 3/2012 |

OTHER PUBLICATIONS

Lavanya et al, The Journal of Immunology, vol. 181, pp. 891-898 (Year: 2008).*
Murphy et al, Journal of Virology, pp. 4601-4609 (Year: 2006).*
Feun, LG et al., "Arginine deprivation in cancer therapy," Current Opinion in Clinical Nutrition and Metabolic Care. Jan. 2015; 18(1):78-82.
Qiu, F et al., "Targeting arginine metabolism pathway to treat arginine-dependent cancers," Cancer Letters. Aug. 1, 2015;364(1):1-7.
Closs, EI et al., "Plasma membrane transporters for arginine," The Journal of Nutrition, Oct. 2004;134(10 Suppl):2752S-2759S; discussion 2765S-2767S.
Boonstra, MC et al., "uPAR-targeted multimodal tracer for pre- and intraoperative imaging in cancer surgery," Oncotarget. Jun. 10, 2015;6(16):14260-73.
Albritton, L M et al., "Envelope-binding domain in the cationic amino acid transporter determines the host range of ecotropic murine retroviruses," Journal of Virololgy, Apr. 1993; 67(4): 2091-2096.
International Search Report for Application No. PCT/EP2016/078163 dated Mar. 31, 2017.
Ban et al., "Isolation and characterization of a 2.3-kilobase-pair cDNA fragment encoding the binding domain of the bovine leukemia virus cell receptor," J Virol. Feb. 1993;67(2):1050-7.

(Continued)

*Primary Examiner* — D. L. Jones
(74) *Attorney, Agent, or Firm* — Nixon & Vanderhye

(57) ABSTRACT

Disclosed are methods for diagnosing CAT1-related diseases, wherein the methods include detecting CAT1 in a cell by a BLV.RBD ligand, or a variant or a fragment thereof. Also disclosed is a BLV.RBD ligand, or a variant or a fragment thereof for use in the treatment of CAT1-related diseases and/or BLV infections.

9 Claims, 3 Drawing Sheets

Specification includes a Sequence Listing.

(56) References Cited

OTHER PUBLICATIONS

Lavanya et al., "Cell surface expression of the bovine leukemia virus-binding receptor on B and T lymphocytes is induced by receptor engagement," J Immunol. Jul. 15, 2008;181(2):891-8.
Suzuki et al., "The mouse homolog of the bovine leukemia virus receptor is closely related to the delta subunit of adaptor-related protein complex AP-3, not associated with the cell surface," J Virol. Jan. 1998;72(1):593-9.

* cited by examiner

SEQUENCE LISTING

```
<160> NUMBER OF SEQ ID NOS: 49

<210> SEQ ID NO 1
<211> LENGTH: 629
<212> TYPE: PRT
<213> ORGANISM: Homo sapiens
<220> FEATURE:
<223> OTHER INFORMATION: CAT1 amino acid sequence

<400> SEQUENCE: 1

Met Gly Cys Lys Val Leu Leu Asn Ile Gly Gln Gln Met Leu Arg Arg
1               5                   10                  15

Lys Val Val Asp Cys Ser Arg Glu Glu Thr Arg Leu Ser Arg Cys Leu
            20                  25                  30

Asn Thr Phe Asp Leu Val Ala Leu Gly Val Gly Ser Thr Leu Gly Ala
        35                  40                  45

Gly Val Tyr Val Leu Ala Gly Ala Val Ala Arg Glu Asn Ala Gly Pro
    50                  55                  60

Ala Ile Val Ile Ser Phe Leu Ile Ala Ala Leu Ala Ser Val Leu Ala
65                  70                  75                  80

Gly Leu Cys Tyr Gly Glu Phe Gly Ala Arg Val Pro Lys Thr Gly Ser
                85                  90                  95

Ala Tyr Leu Tyr Ser Tyr Val Thr Val Gly Glu Leu Trp Ala Phe Ile
            100                 105                 110
```

-continued

```
Thr Gly Trp Asn Leu Ile Leu Ser Tyr Ile Ile Gly Thr Ser Ser Val
        115                 120                 125

Ala Arg Ala Trp Ser Ala Thr Phe Asp Glu Leu Ile Gly Arg Pro Ile
    130                 135                 140

Gly Glu Phe Ser Arg Thr His Met Thr Leu Asn Ala Pro Gly Val Leu
145                 150                 155                 160

Ala Glu Asn Pro Asp Ile Phe Ala Val Ile Ile Ile Leu Ile Leu Thr
                165                 170                 175

Gly Leu Leu Thr Leu Gly Val Lys Glu Ser Ala Met Val Asn Lys Ile
            180                 185                 190

Phe Thr Cys Ile Asn Val Leu Val Leu Gly Phe Ile Met Val Ser Gly
        195                 200                 205

Phe Val Lys Gly Ser Val Lys Asn Trp Gln Leu Thr Glu Glu Asp Phe
    210                 215                 220

Gly Asn Thr Ser Gly Arg Leu Cys Leu Asn Asn Asp Thr Lys Glu Gly
225                 230                 235                 240

Lys Pro Gly Val Gly Gly Phe Met Pro Phe Gly Phe Ser Gly Val Leu
                245                 250                 255

Ser Gly Ala Ala Thr Cys Phe Tyr Ala Phe Val Gly Phe Asp Cys Ile
            260                 265                 270

Ala Thr Thr Gly Glu Glu Val Lys Asn Pro Gln Lys Ala Ile Pro Val
        275                 280                 285

Gly Ile Val Ala Ser Leu Leu Ile Cys Phe Ile Ala Tyr Phe Gly Val
    290                 295                 300

Ser Ala Ala Leu Thr Leu Met Met Pro Tyr Phe Cys Leu Asp Asn Asn
305                 310                 315                 320

Ser Pro Leu Pro Asp Ala Phe Lys His Val Gly Trp Glu Gly Ala Lys
                325                 330                 335

Tyr Ala Val Ala Val Gly Ser Leu Cys Ala Leu Ser Ala Ser Leu Leu
            340                 345                 350

Gly Ser Met Phe Pro Met Pro Arg Val Ile Tyr Ala Met Ala Glu Asp
        355                 360                 365

Gly Leu Leu Phe Lys Phe Leu Ala Asn Val Asn Asp Arg Thr Lys Thr
    370                 375                 380

Pro Ile Ile Ala Thr Leu Ala Ser Gly Ala Val Ala Ala Val Met Ala
385                 390                 395                 400

Phe Leu Phe Asp Leu Lys Asp Leu Val Asp Leu Met Ser Ile Gly Thr
                405                 410                 415

Leu Leu Ala Tyr Ser Leu Val Ala Ala Cys Val Leu Val Leu Arg Tyr
            420                 425                 430

Gln Pro Glu Gln Pro Asn Leu Val Tyr Gln Met Ala Ser Thr Ser Asp
        435                 440                 445

Glu Leu Asp Pro Ala Asp Gln Asn Glu Leu Ala Ser Thr Asn Asp Ser
    450                 455                 460

Gln Leu Gly Phe Leu Pro Glu Ala Glu Met Phe Ser Leu Lys Thr Ile
465                 470                 475                 480

Leu Ser Pro Lys Asn Met Glu Pro Ser Lys Ile Ser Gly Leu Ile Val
                485                 490                 495

Asn Ile Ser Thr Ser Leu Ile Ala Val Leu Ile Ile Thr Phe Cys Ile
            500                 505                 510

Val Thr Val Leu Gly Arg Glu Ala Leu Thr Lys Gly Ala Leu Trp Ala
        515                 520                 525
```

-continued

```
Val Phe Leu Leu Ala Gly Ser Ala Leu Leu Cys Ala Val Val Thr Gly
    530                 535                 540

Val Ile Trp Arg Gln Pro Glu Ser Lys Thr Lys Leu Ser Phe Lys Val
545                 550                 555                 560

Pro Phe Leu Pro Val Leu Pro Ile Leu Ser Ile Phe Val Asn Val Tyr
                565                 570                 575

Leu Met Met Gln Leu Asp Gln Gly Thr Trp Val Arg Phe Ala Val Trp
            580                 585                 590

Met Leu Ile Gly Phe Ile Ile Tyr Phe Gly Tyr Gly Leu Trp His Ser
        595                 600                 605

Glu Glu Ala Ser Leu Asp Ala Asp Gln Ala Arg Thr Pro Asp Gly Asn
    610                 615                 620

Leu Asp Gln Cys Lys
625


<210> SEQ ID NO 2
<211> LENGTH: 1890
<212> TYPE: DNA
<213> ORGANISM: Homo sapiens
<220> FEATURE:
<223> OTHER INFORMATION: CAT1 nucleic acid sequence

<400> SEQUENCE: 2

atggggtgca aagtcctgct caacattggg cagcagatgc tgcggcggaa ggtggtggac      60

tgtagccggg aggagacgcg gctgtctcgc tgcctgaaca cttttgatct ggtggccctc     120

ggggtgggca gcacactggg tgctggtgtc tacgtcctgg ctggagctgt ggcccgtgag     180

aatgcaggcc ctgccattgt catctccttc ctgatcgctg cgctggcctc agtgctggct     240

ggcctgtgct atggcgagtt tggtgctcgg gtccccaaga cgggctcagc ttacctctac     300

agctatgtca ccgttggaga gctctgggcc ttcatcaccg gctggaactt aatcctctcc     360

tacatcatcg gtacttcaag cgtagcgagg gcctggagcg ccaccttcga cgagctgata     420

ggcagaccca tcggggagtt ctcacggaca cacatgactc tgaacgcccc cggcgtgctg     480

gctgaaaacc ccgacatatt cgcagtgatc ataattctca tcttgacagg acttttaact     540

cttggtgtga aagagtcggc catggtcaac aaaatattca cttgtattaa cgtcctggtc     600

ctgggcttca taatggtgtc aggatttgtg aaaggatcgg ttaaaaactg gcagctcacg     660

gaggaggatt ttgggaacac atcaggccgt ctctgtttga acaatgacac aaaagaaggg     720

aagcccggtg ttggtggatt catgcccttc gggttctctg gtgtcctgtc gggggcagcg     780

acttgcttct atgccttcgt gggctttgac tgcatcgcca ccacaggtga agaggtgaag     840

aacccacaga aggccatccc cgtggggatc gtggcgtccc tcttgatctg cttcatcgcc     900

tactttgggg tgtcggctgc cctcacgctc atgatgccct acttctgcct ggacaataac     960

agccccctgc ccgacgcctt taagcacgtg ggctgggaag gtgccaagta cgcagtggcc    1020

gtgggctccc tctgcgctct ttccgccagt cttctaggtt ccatgtttcc catgcctcgg    1080

gttatctatg ccatggctga ggatggactg ctatttaaat tcttagccaa cgtcaatgat    1140

aggaccaaaa caccaataat cgccacatta gcctcgggtg ccgttgctgc tgtgatggcc    1200

ttcctctttg acctgaagga cttggtggac ctcatgtcca ttggcactct cctggcttac    1260

tcgttggtgg ctgcctgtgt gttggtctta cggtaccagc cagagcagcc taacctggta    1320

taccagatgg ccagtacttc cgacgagtta gatccagcag accaaaatga attggcaagc    1380

accaatgatt cccagctggg gtttttacca gaggcagaga tgttctcttt gaaaaccata    1440
```

-continued

```
ctctcaccca aaaacatgga gccttccaaa atctctgggc taattgtgaa catttcaacc   1500

agccttatag ctgttctcat catcaccttc tgcattgtga ccgtgcttgg aagggaggct   1560

ctcaccaaag ggcgctgtg ggcagtcttt ctgctcgcag ggtctgccct cctctgtgcc   1620

gtggtcacgg gcgtcatctg gaggcagccc gagagcaaga ccaagctctc atttaaggtt   1680

cccttcctgc cagtgctccc catcctgagc atcttcgtga acgtctatct catgatgcag   1740

ctggaccagg gcacctgggt ccggtttgct gtgtggatgc tgataggctt catcatctac   1800

tttggctatg gcctgtggca cagcgaggag gcgtccctgg atgccgacca agcaaggact   1860

cctgacggca acttggacca gtgcaagtga                                 1890
```

```
<210> SEQ ID NO 3
<211> LENGTH: 215
<212> TYPE: PRT
<213> ORGANISM: Artificial Sequence
<220> FEATURE:
<223> OTHER INFORMATION: BLV.RBD

<400> SEQUENCE: 3

Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys
    210                 215


<210> SEQ ID NO 4
<211> LENGTH: 181
<212> TYPE: PRT
<213> ORGANISM: Artificial Sequence
<220> FEATURE:
<223> OTHER INFORMATION: BLV.RBD

<400> SEQUENCE: 4

Met Pro Lys Glu Arg Arg Ser Arg Arg Arg Pro Gln Pro Ile Ile Arg
```

-continued

```
1               5                   10                  15

Trp Val Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln
            180
```

<210> SEQ ID NO 5
<211> LENGTH: 549
<212> TYPE: DNA
<213> ORGANISM: Artificial Sequence
<220> FEATURE:
<223> OTHER INFORMATION: BLV.RBD

<400> SEQUENCE: 5

```
accaccatgc ccaaagaacg acggtcccga agacgcccac aaccgatcat cagatggatc     60

tccctcactc ttactctcct cgctctctgt cagcccatcc agacttggag atgctccctg    120

tccctaggaa atcaacaatg gatgacaaca tataaccaag aggcaaaatt tttcatctcc    180

attgaccaaa tactagaggc tcataatcaa tcacctttct gtcccaggtc tcccagatac    240

accttggact ttgtaaatgg ttatcctaag atctattggc ccccccccaca agggcggcgc    300

cggtttggag ccagggccat ggtcacatat gattgcgagc cccgatgccc ttatgtgggg    360

gcagatcact tcgactgccc ccactgggac aatgcctccc aggccgatca aggatccttt    420

tatgtcaatc atcagacttt attcctgcat ctcaaacaat gtcatggaat tttcactcta    480

acctgggaaa tatggggata tgatcccctg atcacttttt ctttacataa aatccctgct    540

ccgccacaa                                                             549
```

<210> SEQ ID NO 6
<211> LENGTH: 21
<212> TYPE: RNA
<213> ORGANISM: Artificial Sequence
<220> FEATURE:
<223> OTHER INFORMATION: siRNA CAT1

<400> SEQUENCE: 6

```
uaauugcacc uuuggcugct t                                               21
```

<210> SEQ ID NO 7

<211> LENGTH: 4329
<212> TYPE: DNA
<213> ORGANISM: Artificial Sequence
<220> FEATURE:
<223> OTHER INFORMATION: H2.RBD tagged with rFc

<400> SEQUENCE: 7
gaattcgagc ttgcatgcct gcaggtcgtt acataactta cggtaaatgg cccgcctggc 60
tgaccgccca acgacccccg cccattgacg tcaataatga cgtatgttcc catagtaacg 120
ccaataggga ctttccattg acgtcaatgg gtggagtatt tacggtaaac tgcccacttg 180
gcagtacatc aagtgtatca tatgccaagt acgcccccta ttgacgtcaa tgacggtaaa 240
tggcccgcct ggcattatgc ccagtacatg accttatggg actttcctac ttggcagtac 300
atctacgtat tagtcatcgc tattaccatg gtgatgcggt tttggcagta catcaatggg 360
cgtggatagc ggtttgactc acggggattt ccaagtctcc accccattga cgtcaatggg 420
agtttgtttt ggcaccaaaa tcaacgggac tttccaaaat gtcgtaacaa ctccgcccca 480
ttgacgcaaa tgggcggtag gcgtgtacgg tgggaggtct atataagcag agctcgttta 540
gtgaaccgtc agatcgcctg gagacgccat ccacgctgtt ttgacctcca tagaagacac 600
cgggaccgat ccagcctccg gactctagag gatccggtac tcgaggaact gaaaaaccag 660
aaagttaact ggtaagttta gtctttttgt cttttatttc aggtcccgga tccggtggtg 720
gtgcaaatca aagaactgct cctcagtgga tgttgccttt acttctaggc ctgtacggaa 780
gtgttacttc tgctctaaaa gctgcggaat tgtacccgcg gccgcaccac catgggtaat 840
gttttcttcc tacttttatt cagtctcaca cattttccac tagcccagca gagccgatgc 900
acactcacga ttggtatctc ctcctaccac tccagcccct gtagcccaac ccaacccgtc 960
tgcacgtgga acctcgacct taattcccta acaacggacc aacgactaca cccccccctgc 1020 cctaacctaa ttacttactc tggcttccat aagacttatt ccttatactt attcccacat 1080
tggataaaaa agccaaacag acagggccta gggtactact cgccttccta caatgaccct 1140
tgctcgctac aatgccccta cttgggctgc caagcatgga catccgcata cacgggcccc 1200
gtctccagtc catcctggaa gtttcattca gatgtaaatt tcacccagga agtcagccaa 1260
gtgtcccttc gactacactt ctctaagtgc ggctcctcca tgaccctcct agtagatgcc 1320
cctggatatg atcctttatg gttcatcacc tcagaaccca ctcagggatc tattgaggga 1380
cgctacccat atgacgtccc ggactacgct tacccgtatg atgttccaga ttatgctcat 1440
caccatcacc atcattgagg ccgcggggat ccagacatga taagatacat tgatgagttt 1500
ggacaaacca caactagaat gcagtgaaaa aaatgcttta tttgtgaaat ttgtgatgct 1560
attgctttat ttgtaaccat tataagctgc aataaacaag ttaacaacaa caattgcatt 1620
cattttatgt ttcaggttca gggggaggtg tgggaggttt tttcggatcc tctagagtcg 1680
acctgcaggc atgcaagctt ggcgtaatca tggtcatagc tgtttcctgt gtgaaattgt 1740
tatccgctca caattccaca caacatacga gccggaagca taaagtgtaa agcctggggt 1800
gcctaatgag tgagctaact cacattaatt gcgttgcgct cactgcccgc tttccagtcg 1860
ggaaacctgt cgtgccagct gcattaatga atcggccaac gcgcggggag aggcggtttg 1920
cgtattgggc gctcttccgc ttcctcgctc actgactcgc tgcgctcggt cgttcggctg 1980
cggcgagcgg tatcagctca ctcaaaggcg gtaatacggt tatccacaga atcaggggat 2040
aacgcaggaa agaacatgtg agcaaaaggc cagcaaaagg ccaggaaccg taaaaaggcc 2100
gcgttgctgg cgtttttcca taggctccgc ccccctgacg agcatcacaa aaatcgacgc 2160

-continued

```
tcaagtcaga ggtggcgaaa cccgacagga ctataaagat accaggcgtt tccccctgga   2220

agctccctcg tgcgctctcc tgttccgacc ctgccgctta ccggatacct gtccgccttt   2280

ctcccttcgg gaagcgtggc gctttctcat agctcacgct gtaggtatct cagttcggtg   2340

taggtcgttc gctccaagct gggctgtgtg cacgaacccc ccgttcagcc cgaccgctgc   2400

gccttatccg gtaactatcg tcttgagtcc aacccggtaa gacacgactt atcgccactg   2460

gcagcagcca ctggtaacag gattagcaga gcgaggtatg taggcggtgc tacagagttc   2520

ttgaagtggt ggcctaacta cggctacact agaaggacag tatttggtat ctgcgctctg   2580

ctgaagccag ttaccttcgg aaaaagagtt ggtagctctt gatccggcaa acaaaccacc   2640

gctggtagcg gtggtttttt tgtttgcaag cagcagatta cgcgcagaaa aaaaggatct   2700

caagaagatc ctttgatctt ttctacgggg tctgacgctc agtggaacga aaactcacgt   2760

taagggattt tggtcatgag attatcaaaa aggatcttca cctagatcct tttaaattaa   2820

aaatgaagtt ttaaatcaat ctaaagtata tatgagtaaa cttggtctga cagttaccaa   2880

tgcttaatca gtgaggcacc tatctcagcg atctgtctat ttcgttcatc catagttgcc   2940

tgactccccg tcgtgtagat aactacgata cgggagggct taccatctgg ccccagtgct   3000

gcaatgatac cgcgagaccc acgctcaccg gctccagatt tatcagcaat aaaccagcca   3060

gccggaaggg ccgagcgcag aagtggtcct gcaactttat ccgcctccat ccagtctatt   3120

aattgttgcc gggaagctag agtaagtagt tcgccagtta atagtttgcg caacgttgtt   3180

gccattgcta caggcatcgt ggtgtcacgc tcgtcgtttg gtatggcttc attcagctcc   3240

ggttcccaac gatcaaggcg agttacatga tcccccatgt tgtgcaaaaa agcggttagc   3300

tccttcggtc ctccgatcgt tgtcagaagt aagttggccg cagtgttatc actcatggtt   3360

atggcagcac tgcataattc tcttactgtc atgccatccg taagatgctt ttctgtgact   3420

ggtgagtact caaccaagtc attctgagaa tagtgtatgc ggcgaccgag ttgctcttgc   3480

ccggcgtcaa tacgggataa taccgcgcca catagcagaa ctttaaaagt gctcatcatt   3540

ggaaaacgtt cttcggggcg aaaactctca aggatcttac cgctgttgag atccagttcg   3600

atgtaaccca ctcgtgcacc caactgatct tcagcatctt ttactttcac cagcgtttct   3660

gggtgagcaa aaacaggaag gcaaaatgcc gcaaaaaagg gaataagggc gacacggaaa   3720

tgttgaatac tcatactctt cctttttcaa tattattgaa gcatttatca gggttattgt   3780

ctcatgagcg gatacatatt tgaatgtatt tagaaaaata aacaaatagg ggttccgcgc   3840

acatttcccc gaaaagtgcc acctgacgtc taagaaacca ttattatcat gacattaacc   3900

tataaaaata ggcgtatcac gaggcccttt cgtctcgcgc gtttcggtga tgacggtgaa   3960

aacctctgac acatgcagct cccggagacg gtcacagctt gtctgtaagc ggatgccggg   4020

agcagacaag cccgtcaggg cgcgtcagcg ggtgttggcg ggtgtcgggg ctggcttaac   4080

tatgcggcat cagagcagat tgtactgaga gtgcaccata tgcggtgtga aataccgcac   4140

agatgcgtaa ggagaaaata ccgcatcagg cgccattcgc cattcaggct gcgcaactgt   4200

tgggaagggc gatcggtgcg ggcctcttcg ctattacgcc agctggcgaa agggggatgt   4260

gctgcaaggc gattaagttg ggtaacgcca gggttttccc agtcacgacg ttgtaaaacg   4320

acggccagt                                                            4329
```

<210> SEQ ID NO 8
<211> LENGTH: 228
<212> TYPE: PRT

<213> ORGANISM: Artificial Sequence
<220> FEATURE:
<223> OTHER INFORMATION: Rabbit Fc fragment

<400> SEQUENCE: 8

Ala Pro Ser Thr Cys Ser Lys Pro Thr Cys Pro Pro Pro Glu Leu Leu
1               5                   10                  15

Gly Gly Pro Ser Val Phe Ile Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Asp Asp Pro Glu Val Gln Phe Thr Trp Tyr Ile Asn Asn Glu Gln
    50                  55                  60

Val Arg Thr Ala Arg Pro Pro Leu Arg Glu Gln Gln Phe Asp Cys Thr
65                  70                  75                  80

Ile Arg Val Val Ser Thr Leu Pro Ile Ala His Gln Asp Trp Leu Arg
                85                  90                  95

Gly Lys Glu Phe Lys Cys Lys Val His Asn Lys Ala Leu Pro Ala Pro
            100                 105                 110

Ile Glu Lys Thr Ile Ser Lys Ala Arg Gly Gln Pro Leu Glu Pro Lys
        115                 120                 125

Val Tyr Thr Met Gly Pro Pro Arg Glu Glu Leu Ser Ser Arg Ser Val
    130                 135                 140

Ser Leu Thr Cys Met Ile Asn Gly Phe Tyr Pro Ser Asp Ile Ser Val
145                 150                 155                 160

Glu Trp Glu Lys Asn Gly Lys Ala Glu Asp Asn Tyr Lys Thr Thr Pro
                165                 170                 175

Ala Val Leu Asp Ser Asp Gly Ser Tyr Phe Leu Tyr Ser Lys Leu Ser
            180                 185                 190

Val Pro Thr Ser Glu Trp Gln Arg Gly Asp Val Phe Thr Cys Ser Val
        195                 200                 205

Met His Glu Ala Leu His Asn His Tyr Thr Gln Lys Ser Ile Ser Arg
    210                 215                 220

Ser Pro Gly Lys
225

<210> SEQ ID NO 9
<211> LENGTH: 687
<212> TYPE: DNA
<213> ORGANISM: Artificial Sequence
<220> FEATURE:
<223> OTHER INFORMATION: Rabbit Fc fragment

<400> SEQUENCE: 9
gcaccctcga catgcagcaa gcccacgtgc ccaccccctg aactcctggg gggaccgtct 60
gtcttcatct tcccccaaa acccaaggac accctcatga tctcacgcac ccccgaggtc 120
acatgcgtgg tggtggacgt gagccaggat gaccccgagg tgcagttcac atggtacata 180
aacaacgagc aggtgcgcac cgcccggccg ccgctacggg agcagcagtt caacagcacg 240
atccgcgtgg tcagcaccct ccccatcacg caccaggact ggctgagggg caaggagttc 300
aagtgcaaag tccacaacaa ggcactcccg gcccccatcg agaaaaccat ctccaaagcc 360
agagggcagc ccctggagcc gaaggtctac accatgggcc ctccccggga ggagctgagc 420
agcaggtcgg tcagcctgac ctgcatgatc aacggcttct acccttccga catctcggtg 480
gagtgggaga agaacgggaa ggcagaggac aactacaaga ccacgccggc cgtgctggac 540
agcgacggct cctacttcct ctacaacaag ctctcagtgc ccacgagtga gtggcagcgg 600
ggcgacgtct tcacctgctc cgtgatgcac gaggccttgc acaaccacta cacgcagaag 660
tccatctccc gctctccggg taaatga 687

<210> SEQ ID NO 10
<211> LENGTH: 229
<212> TYPE: PRT
<213> ORGANISM: Artificial Sequence
<220> FEATURE:
<223> OTHER INFORMATION: Mouse Fc fragment

<400> SEQUENCE: 10

```
Val Asp Val Pro Arg Asp Cys Gly Cys Lys Pro Cys Ile Cys Thr Val
1               5                   10                  15

Pro Glu Val Ser Ser Val Phe Ile Phe Pro Pro Lys Pro Lys Asp Val
            20                  25                  30

Leu Thr Ile Thr Leu Thr Pro Lys Val Thr Cys Val Val Val Asp Ile
        35                  40                  45

Ser Lys Asp Asp Pro Glu Val Gln Phe Ser Trp Phe Val Asp Asp Val
    50                  55                  60

Glu Val His Thr Ala Gln Thr Gln Pro Arg Glu Glu Gln Phe Asn Ser
65                  70                  75                  80

Thr Phe Arg Ser Val Ser Glu Leu Pro Ile Met His Gln Asp Trp Leu
                85                  90                  95

Asn Gly Lys Glu Phe Lys Cys Arg Val Asn Ser Ala Ala Phe Pro Ala
            100                 105                 110

Pro Ile Glu Lys Thr Ile Ser Lys Thr Lys Gly Arg Pro Lys Ala Pro
        115                 120                 125

Gln Val Tyr Thr Ile Pro Pro Pro Lys Glu Gln Met Ala Lys Asp Lys
    130                 135                 140

Val Ser Leu Thr Cys Met Ile Thr Asp Phe Phe Pro Glu Asp Ile Thr
145                 150                 155                 160

Val Glu Trp Gln Trp Asn Gly Gln Pro Ala Glu Asn Tyr Lys Asn Thr
                165                 170                 175

Gln Pro Ile Met Asp Thr Asp Gly Ser Tyr Phe Val Tyr Ser Lys Leu
            180                 185                 190

Asn Val Gln Lys Ser Asn Trp Glu Ala Gly Asn Thr Phe Thr Cys Ser
        195                 200                 205

Val Leu His Glu Gly Leu His Asn His His Thr Glu Lys Ser Leu Ser
    210                 215                 220

His Ser Pro Gly Lys
225
```

<210> SEQ ID NO 11
<211> LENGTH: 690
<212> TYPE: DNA
<213> ORGANISM: Artificial Sequence
<220> FEATURE:
<223> OTHER INFORMATION: Mouse Fc fragment

<400> SEQUENCE: 11
gtcgacgtgc ccagggattg tggttgtaag ccttgcatat gtacagtccc agaagtatca 60
tctgtcttca tcttcccccc aaagcccaag gatgtgctca ccattactct gactcctaag 120
gtcacgtgtg ttgtggtaga catcagcaag gatgatcccg aggtccagtt cagctggttt 180
gtagatgatg tggaggtgca cacagctcag acgcaacccc gggaggagca gttcaacagc 240

-continued

```
actttccgct cagtcagtga acttcccatc atgcaccagg actggctcaa tggcaaggag    300

ttcaaatgca gggtcaacag tgcagctttc cctgccccca tcgagaaaac catctccaaa    360

accaaaggca gaccgaaggc tccacaggtg tacaccattc cacctcccaa ggagcagatg    420

gccaaggata aagtcagtct gacctgcatg ataacagact tcttccctga agacattact    480

gtggagtggc agtggaatgg gcagccagcg gagaactaca agaacactca gcccatcatg    540

gacacagatg gctcttactt cgtctacagc aagctcaatg tgcagaagag caactgggag    600

gcaggaaata ctttcacctg ctctgtgtta catgagggcc tgcacaacca ccatactgag    660

aagagcctct cccactctcc tggtaaatga                                     690
```

<210> SEQ ID NO 12
<211> LENGTH: 1242
<212> TYPE: DNA
<213> ORGANISM: Artificial Sequence
<220> FEATURE:
<223> OTHER INFORMATION: BLV.RBD tagged with a rabbit Fc

<400> SEQUENCE: 12

```
accaccatgc ccaaagaacg acggtcccga agacgcccac aaccgatcat cagatggatc     60

tccctcactc ttactctcct cgctctctgt cagcccatcc agacttggag atgctccctg    120

tccctaggaa atcaacaatg gatgacaaca tataaccaag aggcaaaatt tttcatctcc    180

attgaccaaa tactagaggc tcataatcaa tcacctttct gtcccaggtc tcccagatac    240

accttggact ttgtaaatgg ttatcctaag atctattggc ccccccccaca agggcggcgc    300

cggtttggag ccagggccat ggtcacatat gattgcgagc cccgatgccc ttatgtgggg    360

gcagatcact tcgactgccc ccactgggac aatgcctccc aggccgatca aggatccttt    420

tatgtcaatc atcagacttt attcctgcat ctcaaacaat gtcatggaat tttcactcta    480

acctgggaaa tatggggata tgatcccctg atcacttttt ctttacataa aatccctgct    540

ccgccacaag gatccgcacc ctcgacatgc agcaagccca cgtgcccacc ccctgaactc    600

ctgggggggac cgtctgtctt catcttcccc ccaaaaccca aggacaccct catgatctca    660

cgcacccccg aggtcacatg cgtggtggtg gacgtgagcc aggatgaccc cgaggtgcag    720

ttcacatggt acataaacaa cgagcaggtg cgcaccgccc ggccgccgct acgggagcag    780

cagttcgact gcacgatccg cgtggtcagc accctcccca tcgcgcacca ggactggctg    840

aggggcaagg agttcaagtg caaagtccac aacaaggcac tcccggcccc catcgagaaa    900

accatctcca aagccagagg gcagcccctg gagccgaagg tctacaccat gggccctccc    960

cgggaggagc tgagcagcag gtcggtcagc ctgacctgca tgatcaacgg cttctaccct   1020

tccgacatct cggtggagtg ggagaagaac gggaaggcag aggacaacta caagaccacg   1080

ccggccgtgc tggacagcga cggctcctac ttcctctaca gcaagctctc agtgcccacg   1140

agtgagtggc agcggggcga cgtcttcacc tgctccgtga tgcacgaggc cttgcacaac   1200

cactacacgc agaagtccat ctcccgctct ccgggtaaat ga                      1242
```

<210> SEQ ID NO 13
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 13

```
Met Pro Lys Glu Arg Arg Ser Arg Arg Arg Pro Gln Pro Ile Ile Arg
```

-continued

```
1               5                   10                  15

Trp Val Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430
```

```
Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515


<210> SEQ ID NO 14
<211> LENGTH: 1545
<212> TYPE: DNA
<213> ORGANISM: Artificial Sequence
<220> FEATURE:
<223> OTHER INFORMATION: Nucleic acid sequence of BLV envelope

<400> SEQUENCE: 14

atgcccaaag aacgacggtc ccgaagacgc ccacaaccga tcatcagatg ggtaagtctc     60

actcttactc tcctcgctct ctgtcagccc atccagactt ggagatgctc cctgtcccta    120

ggaaatcaac aatggatgac aacatataac caagaggcaa aatttttcat ctccattgac    180

caaatactag aggctcataa tcaatcacct ttctgtccca ggtctcccag atacaccttg    240

gactttgtaa atggttatcc taagatctat tggccccccc cacaagggcg gcgccggttt    300

ggagccaggg ccatggtcac atatgattgc gagccccgat gcccttatgt gggggcagat    360

cacttcgact gcccccactg ggacaatgcc tcccaggccg atcaagggtc cttttatgtc    420

aatcatcaga ctttattcct gcatctcaaa caatgtcatg gaattttcac tctaacctgg    480

gaaatatggg gatatgatcc cctgatcacc ttttctttac ataaaatccc tgatccccct    540

caacccgact tccctcagct gaacagtgac tgggttccct ctgtcagatc atgggccctg    600

cttttaaatc aaacggcacg ggccttccca gactgtgcta tatgttggga accctcccct    660

ccctgggctc ccgaaatatt agtatataac aaaaccatct ccagctctgg acccggtctc    720

gccctcccgg acgcccaaat cttctgggtc aacacgtcct tgtttaacac cacccaagga    780

tggcaccacc cttcccagag gttgttgttc aacgtttctc aaggcaacgc cttattattg    840

ccccctatct ccctggttaa tctctctacg gcttcctccg cccctcctac ccgggtcaga    900

cgcagtcccg tcgcagccct gaccttaggc ctagccctgt cagtggggct cactggaatt    960

aatgtagccg tgtctgccct tagccatcag agactcacct ccctgatcca cgttctggag   1020

caagatcagc aacgcttgat cacagcaatt aaccagaccc actataattt gcttaatgtg   1080

gcctctgtgg tcgcccagaa ccgacggggg cttgattggt tgtacatccg gctgggtttt   1140

caaagtctat gtcccacaat caatgaacct tgctgtttcc tgcgcatcca aaatgactcc   1200

attatccgcc tcggtgatct ccagcctctc tcgcaaagag tctctacaga ctggcagtgg   1260

ccctggaatt gggatctggg gctcaccgcc tgggtgcggg aaaccattca ttctgttcta   1320

agcctattcc tattagccct ttttttgctc ttcttggccc cctgcctgat aaaatgcctg   1380

acctctcgcc ttttaaaact cctccggcag gctccccact tccctgaaat ctccttcccc   1440

cctaaacccg attctgatta tcaggccttg ctaccgtctg cgccagagat ctactctcac   1500
```

-continued ctctccccca ccaaacccga ttacatcaac cttcgaccct gccct 1545

<210> SEQ ID NO 15
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 15

```
Met Pro Lys Lys Arg Arg Ser Arg Arg Arg Pro Gln Pro Ile Ile Arg
1               5                   10                  15

Trp Val Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
```

-continued

```
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515


<210> SEQ ID NO 16
<211> LENGTH: 1545
<212> TYPE: DNA
<213> ORGANISM: Artificial Sequence
<220> FEATURE:
<223> OTHER INFORMATION: Nucleic acid sequence of BLV envelope

<400> SEQUENCE: 16

atgcctaaaa aacgacggtc ccgaagacgc ccacaaccga tcatcagatg ggtaagtctc     60

actctcactc tcctcgctct ctgtcggccc atccagactt ggagatgctc cctgtcccta    120

ggaaaccaac aatggatgac agcatataac caagaggcaa aattttccat ctccattgac    180

caaatactag aggctcataa tcagtcacct ttctgtgcca agtctcccag atacaccttg    240

gactctgtaa atggctatcc taagatctac tggccccccc cacaagggcg gcgccggttt    300

ggagccaggg ccatggtcac atatgattgc gagccccgat gcccttatgt gggggcagat    360

cgcttcgact gcccccactg ggacaatgcc tcccaggccg atcaaggatc cttttatgtc    420

aatcatcaga ttttattcct gcatcttaaa caatgtcatg gaattttcac tctaacctgg    480

gagatatggg gatatgatcc cctgatcacc ttttctttac ataagatccc tgatcccccct   540

caacccgact ttccccagtt gaacagtgac tgggttccct ctgtcagatc atgggccctg    600

cttttaaacc aaacagcacg ggccttccca gactgtgcta tatgttggga accttcccct    660

ccctgggctc ccgaaatatt agtatataac aaaaccatct ccagctctgg acccggcctc    720

gccctcccgg acgcccaaat cttctgggtc aacacgtcct cgtttaacac cacccaagga    780

tggcaccacc cttcccagag gttgttgttc aatgtttctc aaggcaacgc cttgttatta    840

cctcctatct ccctggttaa tctctctacg gcttcctccg cccctcctac ccgggtcaga    900

cgtagtcccg tcgcagccct gaccttaggc ctagccctgt cagtggggct cactggaatt    960

aatgtggccg tgtctgccct tagccatcag agactcacct ccctgatcca cgttctggag   1020

caagatcagc aacgcttgat cacagcaatt aaccagaccc actataattt gcttaatgtg   1080

gcctctgtgg ttgcccagaa ccgacggggg cttgattggt tgtacatccg gctgggtttt   1140
```

```
caaagcctat gtcccacaat taatgagcct tgctgtttcc tgcgcattca aaatgactcc   1200

attatccgcc tcggtgatct ccagcctctc tcgcaaagag tctctacaga ctggcagtgg   1260

ccctggaatt gggatctggg gctcactgcc tgggtgcgag aaaccattca ttctgttcta   1320

agcctgttcc tattagccct ttttttgctc ttcctggccc cctgcctgat aaaatgcttg   1380

acctctcgcc ttttaaagct cctccggcag gctccccact tccctgaaat ctccttaacc   1440

cctaaacccg attctgatta tcaggccttg ctaccatctg caccagagat ctactctcac   1500

ctctcccccg tcaaacccga ttacatcaac ctccgaccct gccct                    1545
```

<210> SEQ ID NO 17
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 17

```
Met Pro Lys Glu Arg Arg Ser Arg Arg Arg Pro Gln Pro Ile Ile Arg
1               5                   10                  15

Trp Val Ser Leu Thr Leu Thr Leu Leu Ser Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Ser Ile Ala Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Asn Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285
```

-continued

```
Ser Thr Ala Ser Ser Ala Pro Pro Thr Arg Val Arg Arg Ser Pro Ala
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Ala
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515
```

<210> SEQ ID NO 18
<211> LENGTH: 1545
<212> TYPE: DNA
<213> ORGANISM: Artificial Sequence
<220> FEATURE:
<223> OTHER INFORMATION: Nucleic acid sequence of BLV envelope

<400> SEQUENCE: 18

```
atgcccaaag aacgacggtc ccgaagacgc ccacaaccga tcatcagatg ggtaagtctc      60

actcttactc tcctctctct ctgtcagccc atccagactt ggagatgctc cctgtcccta     120

ggaaatcaac aatggatgac aacatataac caagaggcaa aattttccat cgccattgac     180

caaatactag aggctcataa tcaatcgcct ttctgtccca ggtctcccag atacaccttg     240

gactttgtaa atggttatcc taagatctat tggcccccccc cacaagggcg acgccggttt     300

ggagccaggg ccatggtcac atatgattgc gagccccgat gcccttatgt gggggcagat     360

cacttcgact gccccccactg ggacaatgct tcccaggccg atcaagggtc cttttatgtc     420

aatcatcaga ttttattcct gcatctcaaa caatgtcatg gaattttcac tctaacctgg     480

gaaatatggg gatatgatcc cctgatcacc ttttctttac ataaaatccc tgatccccct     540

caacccgact tccctcagct gaacagtgac tgggttccct ctgtcaggtc atgggccctg     600

cttttaaatc aaacggcacg ggccttccca gactgtgcta tatgttggga accttcccct     660

ccctgggctc ccgaaatatt agtatataac aaaaccatct ccaactctgg acccggtctc     720
```

-continued

```
gccctcccgg acgcccaaat cttctgggtc aacacgtcct tgtttaacac cacccaagga    780

tggcaccacc cttcccagag gttgttgttc aacgtttctc aaggcaacgc cttattatta    840

ccccctatct ccctggttaa tctctctacg gcttcctccg cccctcctac ccgggtcaga    900

cgcagtcctg ccgcagccct gaccttgggc ctagccctgt cagtggggct cactggaatt    960

aatgtagccg tgtccgccct tagccatcag agactcacct ccctgatcca cgttctggag   1020

caagatcagc aacgcttgat cacagcaatt aaccagaccc actataattt gcttaatgtg   1080

gcctctgtgg tcgcccagaa ccgacggggg cttgattggt tgtacatccg gctgggtttt   1140

caaagcctat gtcccacgat caatgaacct tgctgtttcc tgcgcattca aaatgactcc   1200

attatccgcc tcggtgatct ccagcctctc tcgcaaagag tctctacaga ctggcaatgg   1260

ccctggaatt gggatctggg gctcaccgcc tgggtgcgag aaaccattca ttctgttcta   1320

agcctattcc tattagccct ttttttgctc ttcttggccc cctgcctgat aaaatgcttg   1380

acctctcgcc ttttaaaact cctccggcag gctccccact tccctgaaat ctccttggcc   1440

cctaaacccg attctgatta tcaggccttg ctaccatccg cgccagagat ctactctcac   1500

ctctccccca ccaaacccga ttacatcaac cttcgaccct gccct                   1545
```

<210> SEQ ID NO 19
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 19

```
Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Lys Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220
```

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515

<210> SEQ ID NO 20
<211> LENGTH: 1545
<212> TYPE: DNA
<213> ORGANISM: Artificial Sequence
<220> FEATURE:
<223> OTHER INFORMATION: Nucleic acid sequence BLV envelope

<400> SEQUENCE: 20
atgcctaaag aacgacggtc ccgaagacgc ccacaaccga tcatcagatg ggtaagtctc      60
actctcactc tcctcgctct ctgtcggccc atccagactt ggagatgctc cctgtcccta     120
ggaaaccaac aatggatgac agcatataac caagaggcaa aattttccat ctccattgac     180
caaatactag aggctcataa tcagtcacct ttctgtgcca agtctcccag atacaccttg 240
gactctgtaa atggctatcc taagatctac tggccccccc caaaagggcg gcgccggttt 300
ggagccaggg ccatggtcac atatgattgc gagccccgat gcccttatgt gggggcagat 360

```
cgcttcgact gcccccactg ggacaatgcc tcccaggccg atcaaggatc cttttatgtc    420

aatcatcaga ttttattcct gcatctcaaa caatgtcatg gaattttcac cctaacctgg    480

gagatatggg gatatgatcc cctgatcacc ttttctttac ataagattcc tgatccccct    540

caacccgact ttccccagtt gaacagtgac tgggttccct ctgtcagatc atgggccctg    600

cttttaaatc aaacagcacg ggccttccca gactgtgcta tatgttggga accttcccct    660

ccctgggctc ccgaaatatt agtatataac aaaaccatct ccagctctgg acccggcctc    720

gccctcccgg acgcccaaat cttctgggtc aacacgtcct cgtttaacac cacccaagga    780

tggcaccacc cttcccagag gttgttgttc aatgtttctc aaggcaacgc cttgttatta    840

cctcctatct ccctggttaa tctctctacg gcttcctccg cccctcctac ccgggtcaga    900

cgtagtcccg tcgcagccct gaccttaggc ctagccctgt cagtggggct cactggaatt    960

aatgtggccg tgtctgccct tagccatcag agactcacct ccctgatcca cgttctggag   1020

caggatcagc aacgcttgat cacagcaatt aaccagaccc actataattt gcttaatgtg   1080

gcctctgtgg ttgcccagaa ccgacggggg cttgattggt tgtacatccg gctgggtttt   1140

caaagcctat gtcccacaat taatgagcct tgctgtttcc tgcgcattca aaatgactcc   1200

attatccgcc tcggtgatct ccagcctctc tcgcaaagag tctctacaga ctggcagtgg   1260

ccctggaatt gggatctggg gctcactgcc tgggtgcgag aaaccattca ttctgttcta   1320

agcctgttcc tattagccct ttttttgctc ttcctggccc cctgcctgat aaaatgcttg   1380

acctctcgcc ttttaaagct cctccggcag gctccccact tccctgaaat ctccttaacc   1440

cctaaacccg attctgacta tcaggccttg ctaccatctg caccagagat ctactctcac   1500

ctctccccg tcaaacccga ttacatcaac ctccgaccct gccct                    1545
```

<210> SEQ ID NO 21
<211> LENGTH: 181
<212> TYPE: PRT
<213> ORGANISM: Artificial Sequence
<220> FEATURE:
<223> OTHER INFORMATION: BLV.RBD

<400> SEQUENCE: 21

```
Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
```

-continued 145 150 155 160

Glu Ile Trp Gly Tyr Asp Pro Leu Ile Thr Phe Ser Leu His Lys Ile
165 170 175

Pro Ala Pro Pro Gln
180

<210> SEQ ID NO 22
<211> LENGTH: 543
<212> TYPE: DNA
<213> ORGANISM: Artificial Sequence
<220> FEATURE:
<223> OTHER INFORMATION: BLV.RBD

<400> SEQUENCE: 22
atgcccaaag aacgacggtc ccgaagacgc ccacaaccga tcatcagatg gatctccctc 60
actcttactc tcctcgctct ctgtcagccc atccagactt ggagatgctc cctgtcccta 120
ggaaatcaac aatggatgac aacatataac caagaggcaa aatttttcat ctccattgac 180
caaatactag aggctcataa tcaatcacct ttctgtccca ggtctcccag atacaccttg 240
gactttgtaa atggttatcc taagatctat tggccccccc cacaagggcg gcgccggttt 300
ggagccaggg ccatggtcac atatgattgc gagccccgat gcccttatgt gggggcagat 360
cacttcgact gcccccactg ggacaatgcc tcccaggccg atcaaggatc cttttatgtc 420
aatcatcaga ctttattcct gcatctcaaa caatgtcatg gaattttcac tctaacctgg 480
gaaatatggg gatatgatcc cctgatcact tttctcttac ataaaatccc tgctccgcca 540
caa 543

<210> SEQ ID NO 23
<211> LENGTH: 622
<212> TYPE: PRT
<213> ORGANISM: Mus musculus
<220> FEATURE:
<223> OTHER INFORMATION: CAT1 amino acid sequence

<400> SEQUENCE: 23

Met Gly Cys Lys Asn Leu Leu Gly Leu Gly Gln Gln Met Leu Arg Arg
1 5 10 15

Lys Val Val Asp Cys Ser Arg Glu Glu Ser Arg Leu Ser Arg Cys Leu
20 25 30

Asn Thr Tyr Asp Leu Val Ala Leu Gly Val Gly Ser Thr Leu Gly Ala
35 40 45

Gly Val Tyr Val Leu Ala Gly Ala Val Ala Arg Glu Asn Ala Gly Pro
50 55 60

Ala Ile Val Ile Ser Phe Leu Ile Ala Ala Leu Ala Ser Val Leu Ala
65 70 75 80

Gly Leu Cys Tyr Gly Glu Phe Gly Ala Arg Val Pro Lys Thr Gly Ser
85 90 95

Ala Tyr Leu Tyr Ser Tyr Val Thr Val Gly Glu Leu Trp Ala Phe Ile
100 105 110

Thr Gly Trp Asn Leu Ile Leu Ser Tyr Ile Ile Gly Thr Ser Ser Val
115 120 125

Ala Arg Ala Trp Ser Ala Thr Phe Asp Glu Leu Ile Gly Lys Pro Ile
130 135 140

Gly Glu Phe Ser Arg Gln His Met Ala Leu Asn Ala Pro Gly Val Leu
145 150 155 160

Ala Gln Thr Pro Asp Ile Phe Ala Val Ile Ile Ile Ile Ile Leu Thr

-continued

```
                165                 170                 175

Gly Leu Leu Thr Leu Gly Val Lys Glu Ser Ala Met Val Asn Lys Ile
            180                 185                 190

Phe Thr Cys Ile Asn Val Leu Val Leu Cys Phe Ile Val Val Ser Gly
        195                 200                 205

Phe Val Lys Gly Ser Ile Lys Asn Trp Gln Leu Thr Glu Lys Asn Phe
    210                 215                 220

Ser Cys Asn Asn Asn Asp Thr Asn Val Lys Tyr Gly Glu Gly Gly Phe
225                 230                 235                 240

Met Pro Phe Gly Phe Ser Gly Val Leu Ser Gly Ala Ala Thr Cys Phe
                245                 250                 255

Tyr Ala Phe Val Gly Phe Asp Cys Ile Ala Thr Thr Gly Glu Glu Val
            260                 265                 270

Lys Asn Pro Gln Lys Ala Ile Pro Val Gly Ile Val Ala Ser Leu Leu
        275                 280                 285

Ile Cys Phe Ile Ala Tyr Phe Gly Val Ser Ala Ala Leu Thr Leu Met
    290                 295                 300

Met Pro Tyr Phe Cys Leu Asp Ile Asp Ser Pro Leu Pro Gly Ala Phe
305                 310                 315                 320

Lys His Gln Gly Trp Glu Glu Ala Lys Tyr Ala Val Ala Ile Gly Ser
                325                 330                 335

Leu Cys Ala Leu Ser Thr Ser Leu Leu Gly Ser Met Phe Pro Met Pro
            340                 345                 350

Arg Val Ile Tyr Ala Met Ala Glu Asp Gly Leu Leu Phe Lys Phe Leu
        355                 360                 365

Ala Lys Ile Asn Asn Arg Thr Lys Thr Pro Val Ile Ala Thr Val Thr
    370                 375                 380

Ser Gly Ala Ile Ala Ala Val Met Ala Phe Leu Phe Glu Leu Lys Asp
385                 390                 395                 400

Leu Val Asp Leu Met Ser Ile Gly Thr Leu Leu Ala Tyr Ser Leu Val
                405                 410                 415

Ala Ala Cys Val Leu Val Leu Arg Tyr Gln Pro Glu Gln Pro Asn Leu
            420                 425                 430

Val Tyr Gln Met Ala Arg Thr Thr Glu Glu Leu Asp Arg Val Asp Gln
        435                 440                 445

Asn Glu Leu Val Ser Ala Ser Glu Ser Gln Thr Gly Phe Leu Pro Val
    450                 455                 460

Ala Glu Lys Phe Ser Leu Lys Ser Ile Leu Ser Pro Lys Asn Val Glu
465                 470                 475                 480

Pro Ser Lys Phe Ser Gly Leu Ile Val Asn Ile Ser Ala Gly Leu Leu
                485                 490                 495

Ala Ala Leu Ile Ile Thr Val Cys Ile Val Ala Val Leu Gly Arg Glu
            500                 505                 510

Ala Leu Ala Glu Gly Thr Leu Trp Ala Val Phe Val Met Thr Gly Ser
        515                 520                 525

Val Leu Leu Cys Met Leu Val Thr Gly Ile Ile Trp Arg Gln Pro Glu
    530                 535                 540

Ser Lys Thr Lys Leu Ser Phe Lys Val Pro Phe Val Pro Val Leu Pro
545                 550                 555                 560

Val Leu Ser Ile Phe Val Asn Ile Tyr Leu Met Met Gln Leu Asp Gln
                565                 570                 575

Gly Thr Trp Val Arg Phe Ala Val Trp Met Leu Ile Gly Phe Thr Ile
            580                 585                 590
```

```
Tyr Phe Gly Tyr Gly Ile Trp His Ser Glu Glu Ala Ser Leu Ala Ala
        595                 600                 605

Gly Gln Ala Lys Thr Pro Asp Ser Asn Leu Asp Gln Cys Lys
    610                 615                 620


<210> SEQ ID NO 24
<211> LENGTH: 624
<212> TYPE: PRT
<213> ORGANISM: Rattus norvegicus
<220> FEATURE:
<223> OTHER INFORMATION: CAT1 amino acid sequence

<400> SEQUENCE: 24

Met Gly Cys Lys Asn Leu Leu Ser Leu Gly Gln Gln Met Leu Arg Arg
1               5                   10                  15

Lys Val Val Asp Cys Ser Arg Glu Glu Ser Arg Leu Ser Arg Cys Leu
            20                  25                  30

Asn Thr Tyr Asp Leu Val Ala Leu Gly Val Gly Ser Thr Leu Gly Ala
        35                  40                  45

Gly Val Tyr Val Leu Ala Gly Ala Val Ala Arg Glu Asn Ala Gly Pro
    50                  55                  60

Ala Ile Val Ile Ser Phe Leu Ile Ala Ala Leu Ala Ser Val Leu Ala
65                  70                  75                  80

Gly Leu Cys Tyr Gly Glu Phe Gly Ala Arg Val Pro Lys Thr Gly Ser
                85                  90                  95

Ala Tyr Leu Tyr Ser Tyr Val Thr Val Gly Glu Leu Trp Ala Phe Ile
            100                 105                 110

Thr Gly Trp Asn Leu Ile Leu Ser Tyr Ile Ile Gly Thr Ser Ser Val
        115                 120                 125

Ala Arg Ala Trp Ser Ala Thr Phe Asp Glu Leu Ile Gly Lys Pro Ile
    130                 135                 140

Gly Glu Phe Ser Arg Gln His Met Ala Leu Asn Ala Pro Gly Val Leu
145                 150                 155                 160

Ala Gln Thr Pro Asp Ile Phe Ala Val Ile Ile Ile Ile Ile Leu Thr
                165                 170                 175

Gly Leu Leu Thr Leu Gly Val Lys Glu Ser Ala Met Val Asn Lys Ile
            180                 185                 190

Phe Thr Cys Ile Asn Val Leu Val Leu Cys Phe Ile Met Val Ser Gly
        195                 200                 205

Phe Val Lys Gly Ser Ile Glu Asn Trp Gln Leu Thr Glu Asn Lys Ser
    210                 215                 220

Ser Pro Leu Cys Gly Asn Asn Asp Thr Asn Val Lys Tyr Gly Glu Gly
225                 230                 235                 240

Gly Phe Met Pro Phe Gly Phe Ser Gly Val Leu Ser Gly Ala Ala Thr
                245                 250                 255

Cys Phe Tyr Ala Phe Val Gly Phe Asp Cys Ile Ala Thr Thr Gly Glu
            260                 265                 270

Glu Val Lys Asn Pro Gln Lys Ala Ile Pro Val Gly Ile Val Ala Ser
        275                 280                 285

Leu Leu Ile Cys Phe Ile Ala Tyr Phe Gly Val Ser Ala Ala Leu Thr
    290                 295                 300

Leu Met Met Pro Tyr Phe Cys Leu Asp Thr Asp Ser Pro Leu Pro Gly
305                 310                 315                 320

Ala Phe Lys Tyr Arg Gly Trp Glu Glu Ala Lys Tyr Ala Val Ala Val
                325                 330                 335
```

Gly Ser Leu Cys Ala Leu Ser Thr Ser Pro Leu Gly Ser Met Phe Pro
340 345 350

Met Pro Arg Val Ile Tyr Ala Met Ala Glu Asp Gly Leu Leu Phe Lys
355 360 365

Phe Leu Ala Lys Ile Asn Asp Arg Thr Lys Thr Pro Ile Ile Ala Thr
370 375 380

Val Thr Ser Gly Ala Ile Ala Ala Val Met Ala Phe Leu Phe Glu Leu
385 390 395 400

Lys Asp Leu Val Asp Leu Met Ser Ile Gly Thr Leu Leu Ala Tyr Ser
405 410 415

Leu Val Ala Ala Cys Val Leu Val Leu Arg Tyr Gln Pro Glu Gln Pro
420 425 430

Asn Leu Val Tyr Gln Met Ala Arg Thr Thr Asp Glu Leu Asp Gln Val
435 440 445

Asp Gln Asn Glu Met Val Ser Ala Ser Glu Ser Gln Thr Gly Phe Leu
450 455 460

Pro Ala Ala Glu Lys Phe Ser Leu Lys Thr Ile Leu Ser Pro Lys Asn
465 470 475 480

Met Glu Pro Ser Lys Phe Ser Gly Leu Ile Val Asn Ile Ser Ala Gly
485 490 495

Leu Leu Ala Val Leu Ile Ile Thr Val Cys Ile Val Ala Val Leu Gly
500 505 510

Arg Glu Ala Leu Ala Glu Gly Thr Leu Trp Ala Val Phe Val Met Thr
515 520 525

Gly Ser Val Leu Leu Cys Met Leu Val Thr Gly Ile Ile Trp Arg Gln
530 535 540

Pro Glu Ser Lys Thr Lys Leu Ser Phe Lys Val Pro Phe Val Pro Val
545 550 555 560

Leu Pro Val Leu Ser Ile Phe Val Asn Ile Tyr Leu Met Met Gln Leu
565 570 575

Asp Gln Gly Thr Trp Val Arg Phe Ala Val Trp Met Leu Ile Ala Phe
580 585 590

Ala Ile Tyr Phe Gly Tyr Gly Val Trp His Ser Glu Glu Ala Ser Leu
595 600 605

Ala Ala Gly Gln Ala Lys Thr Pro Asp Ser Asn Leu Asp Gln Cys Lys
610 615 620

<210> SEQ ID NO 25
<211> LENGTH: 665
<212> TYPE: PRT
<213> ORGANISM: Moloney murine leukemia virus isolate Shinnick
<220> FEATURE:
<223> OTHER INFORMATION: Envelope glycoprotein

<400> SEQUENCE: 25

Met Ala Arg Ser Thr Leu Ser Lys Pro Leu Lys Asn Lys Val Asn Pro
1 5 10 15

Arg Gly Pro Leu Ile Pro Leu Ile Leu Leu Met Leu Arg Gly Val Ser
20 25 30

Thr Ala Ser Pro Gly Ser Ser Pro His Gln Val Tyr Asn Ile Thr Trp
35 40 45

Glu Val Thr Asn Gly Asp Arg Glu Thr Val Trp Ala Thr Ser Gly Asn
50 55 60

His Pro Leu Trp Thr Trp Trp Pro Asp Leu Thr Pro Asp Leu Cys Met
65 70 75 80

-continued

```
Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
    130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
        195                 200                 205

Cys Lys Asp Asn Lys Trp Cys Asn Pro Leu Val Ile Arg Phe Thr Asp
    210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Leu Gly Pro Arg Val Pro Ile Gly Pro Asn Pro
            260                 265                 270

Val Leu Ala Asp Gln Gln Pro Leu Ser Lys Pro Lys Pro Val Lys Ser
        275                 280                 285

Pro Ser Val Thr Lys Pro Pro Ser Gly Thr Pro Leu Ser Pro Thr Gln
    290                 295                 300

Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
                325                 330                 335

Trp Leu Cys Leu Val Ala Gly Pro Pro Tyr Tyr Glu Gly Val Ala Val
            340                 345                 350

Leu Gly Thr Tyr Ser Asn His Thr Ser Ala Pro Ala Asn Cys Ser Val
        355                 360                 365

Ala Ser Gln His Lys Leu Thr Leu Ser Glu Val Thr Gly Gln Gly Leu
    370                 375                 380

Cys Ile Gly Ala Val Pro Lys Thr His Gln Ala Leu Cys Asn Thr Thr
385                 390                 395                 400

Gln Thr Ser Ser Arg Gly Ser Tyr Tyr Leu Val Ala Pro Thr Gly Thr
                405                 410                 415

Met Trp Ala Cys Ser Thr Gly Leu Thr Pro Cys Ile Ser Thr Thr Ile
            420                 425                 430

Leu Asn Leu Thr Thr Asp Tyr Cys Val Leu Val Glu Leu Trp Pro Arg
        435                 440                 445

Val Thr Tyr His Ser Pro Ser Tyr Val Tyr Gly Leu Phe Glu Arg Ser
    450                 455                 460

Asn Arg His Lys Arg Glu Pro Val Ser Leu Thr Leu Ala Leu Leu Leu
465                 470                 475                 480

Gly Gly Leu Thr Met Gly Gly Ile Ala Ala Gly Ile Gly Thr Gly Thr
                485                 490                 495
```

-continued

```
Thr Ala Leu Met Ala Thr Gln Gln Phe Gln Gln Leu Gln Ala Ala Val
            500                 505                 510

Gln Asp Asp Leu Arg Glu Val Glu Lys Ser Ile Ser Asn Leu Glu Lys
        515                 520                 525

Ser Leu Thr Ser Leu Ser Glu Val Val Leu Gln Asn Arg Arg Gly Leu
    530                 535                 540

Asp Leu Leu Phe Leu Lys Glu Gly Gly Leu Cys Ala Ala Leu Lys Glu
545                 550                 555                 560

Glu Cys Cys Phe Tyr Ala Asp His Thr Gly Leu Val Arg Asp Ser Met
                565                 570                 575

Ala Lys Leu Arg Glu Arg Leu Asn Gln Arg Gln Lys Leu Phe Glu Ser
            580                 585                 590

Thr Gln Gly Trp Phe Glu Gly Leu Phe Asn Arg Ser Pro Trp Phe Thr
        595                 600                 605

Thr Leu Ile Ser Thr Ile Met Gly Pro Leu Ile Val Leu Leu Met Ile
    610                 615                 620

Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
                645                 650                 655

Gln Leu Lys Pro Ile Glu Tyr Glu Pro
            660                 665


<210> SEQ ID NO 26
<211> LENGTH: 675
<212> TYPE: PRT
<213> ORGANISM: Friend murine leukemia virus (ISOLATE 57)
<220> FEATURE:
<223> OTHER INFORMATION: Envelope glycoprotein

<400> SEQUENCE: 26

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His Gln Val Tyr Asn Ile Thr
        35                  40                  45

Trp Glu Val Thr Asn Gly Asp Arg Glu Thr Val Trp Ala Ile Ser Gly
    50                  55                  60

Asn His Pro Leu Trp Thr Trp Trp Pro Val Leu Thr Pro Asp Leu Cys
65                  70                  75                  80

Met Leu Ala Leu Ser Gly Pro Pro His Trp Gly Leu Glu Tyr Gln Ala
                85                  90                  95

Pro Tyr Ser Ser Pro Pro Gly Pro Pro Cys Cys Ser Gly Ser Ser Gly
            100                 105                 110

Ser Ser Ala Gly Cys Ser Arg Asp Cys Asp Glu Pro Leu Thr Ser Leu
        115                 120                 125

Thr Pro Arg Cys Asn Thr Ala Trp Asn Arg Leu Lys Leu Asp Gln Val
    130                 135                 140

Thr His Lys Ser Ser Glu Gly Phe Tyr Val Cys Pro Gly Ser His Arg
145                 150                 155                 160

Pro Arg Glu Ala Lys Ser Cys Gly Gly Pro Asp Ser Phe Tyr Cys Ala
                165                 170                 175

Ser Trp Gly Cys Glu Thr Thr Gly Arg Val Tyr Trp Lys Pro Ser Ser
            180                 185                 190
```

-continued

```
Ser Trp Asp Tyr Ile Thr Val Asp Asn Asn Leu Thr Thr Ser Gln Ala
        195                 200                 205

Val Gln Val Cys Lys Asp Asn Lys Trp Cys Asn Pro Leu Ala Ile Gln
    210                 215                 220

Phe Thr Asn Ala Gly Lys Gln Val Thr Ser Trp Thr Thr Gly His Tyr
225                 230                 235                 240

Trp Gly Leu Arg Leu Tyr Val Ser Gly Arg Asp Pro Gly Leu Thr Phe
                245                 250                 255

Gly Ile Arg Leu Arg Tyr Gln Asn Leu Gly Pro Arg Val Pro Ile Gly
            260                 265                 270

Pro Asn Pro Val Leu Ala Asp Gln Leu Ser Leu Pro Arg Pro Asn Pro
        275                 280                 285

Leu Pro Lys Pro Ala Lys Ser Pro Pro Ala Ser Asn Ser Thr Pro Thr
    290                 295                 300

Leu Ile Ser Pro Ser Pro Thr Pro Thr Gln Pro Pro Pro Ala Gly Thr
305                 310                 315                 320

Gly Asp Arg Leu Leu Asn Leu Val Gln Gly Ala Tyr Gln Ala Leu Asn
                325                 330                 335

Leu Thr Asn Pro Asp Lys Thr Gln Glu Cys Trp Leu Cys Leu Val Ser
            340                 345                 350

Gly Pro Pro Tyr Tyr Glu Gly Val Ala Val Leu Gly Thr Tyr Ser Asn
        355                 360                 365

His Thr Ser Ala Pro Ala Asn Cys Ser Val Ala Ser Gln His Lys Leu
    370                 375                 380

Thr Leu Ser Glu Val Thr Gly Arg Gly Leu Cys Ile Gly Thr Val Pro
385                 390                 395                 400

Lys Thr His Gln Ala Leu Cys Asn Thr Thr Leu Lys Ile Asp Lys Gly
                405                 410                 415

Ser Tyr Tyr Leu Val Ala Pro Thr Gly Thr Thr Trp Ala Cys Asn Thr
            420                 425                 430

Gly Leu Thr Pro Cys Leu Ser Ala Thr Val Leu Asn Arg Thr Thr Asp
        435                 440                 445

Tyr Cys Val Leu Val Glu Leu Trp Pro Arg Val Thr Tyr His Pro Pro
    450                 455                 460

Ser Tyr Val Tyr Ser Gln Phe Glu Lys Ser Tyr Arg His Lys Arg Glu
465                 470                 475                 480

Pro Val Ser Leu Thr Leu Ala Leu Leu Leu Gly Gly Leu Thr Met Gly
                485                 490                 495

Gly Ile Ala Ala Gly Val Gly Thr Gly Thr Thr Ala Leu Val Ala Thr
            500                 505                 510

Gln Gln Phe Gln Gln Leu His Ala Ala Val Gln Asp Asp Leu Lys Glu
        515                 520                 525

Val Glu Lys Ser Ile Thr Asn Leu Glu Lys Ser Leu Thr Ser Leu Ser
    530                 535                 540

Glu Val Val Leu Gln Asn Arg Arg Gly Leu Asp Leu Leu Phe Leu Lys
545                 550                 555                 560

Glu Gly Gly Leu Cys Ala Ala Leu Lys Glu Glu Cys Cys Phe Tyr Ala
                565                 570                 575

Asp His Thr Gly Leu Val Arg Asp Ser Met Ala Lys Leu Arg Glu Arg
            580                 585                 590

Leu Thr Gln Arg Gln Lys Leu Phe Glu Ser Ser Gln Gly Trp Phe Glu
        595                 600                 605

Gly Leu Phe Asn Arg Ser Pro Trp Phe Thr Thr Leu Ile Ser Thr Ile
```

```
    610                 615                 620

Met Gly Pro Leu Ile Ile Leu Leu Leu Ile Leu Leu Phe Gly Pro Cys
625                 630                 635                 640

Ile Leu Asn Arg Leu Val Gln Phe Val Lys Asp Arg Ile Ser Val Val
                645                 650                 655

Gln Ala Leu Val Leu Thr Gln Gln Tyr His Gln Leu Lys Pro Leu Glu
            660                 665                 670

Tyr Glu Pro
        675


<210> SEQ ID NO 27
<211> LENGTH: 412
<212> TYPE: PRT
<213> ORGANISM: Artificial Sequence
<220> FEATURE:
<223> OTHER INFORMATION: BLV.RBD tagged with a mouse Fc

<400> SEQUENCE: 27

Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Gly Ser Val Asp Val Pro Arg Asp Cys Gly Cys
            180                 185                 190

Lys Pro Cys Ile Cys Thr Val Pro Glu Val Ser Ser Val Phe Ile Phe
        195                 200                 205

Pro Pro Lys Pro Lys Asp Val Leu Thr Ile Thr Leu Thr Pro Lys Val
    210                 215                 220

Thr Cys Val Val Val Asp Ile Ser Lys Asp Asp Pro Glu Val Gln Phe
225                 230                 235                 240

Ser Trp Phe Val Asp Asp Val Glu Val His Thr Ala Gln Thr Gln Pro
                245                 250                 255

Arg Glu Glu Gln Phe Asn Ser Thr Phe Arg Ser Val Ser Glu Leu Pro
            260                 265                 270

Ile Met His Gln Asp Trp Leu Asn Gly Lys Glu Phe Lys Cys Arg Val
        275                 280                 285

Asn Ser Ala Ala Phe Pro Ala Pro Ile Glu Lys Thr Ile Ser Lys Thr
```

290 295 300

Lys Gly Arg Pro Lys Ala Pro Gln Val Tyr Thr Ile Pro Pro Pro Lys
305 310 315 320

Glu Gln Met Ala Lys Asp Lys Val Ser Leu Thr Cys Met Ile Thr Asp
325 330 335

Phe Phe Pro Glu Asp Ile Thr Val Glu Trp Gln Trp Asn Gly Gln Pro
340 345 350

Ala Glu Asn Tyr Lys Asn Thr Gln Pro Ile Met Asp Thr Asp Gly Ser
355 360 365

Tyr Phe Val Tyr Ser Lys Leu Asn Val Gln Lys Ser Asn Trp Glu Ala
370 375 380

Gly Asn Thr Phe Thr Cys Ser Val Leu His Glu Gly Leu His Asn His
385 390 395 400

His Thr Glu Lys Ser Leu Ser His Ser Pro Gly Lys
405 410

<210> SEQ ID NO 28
<211> LENGTH: 181
<212> TYPE: PRT
<213> ORGANISM: Artificial Sequence
<220> FEATURE:
<223> OTHER INFORMATION: BLV.RBD

<400> SEQUENCE: 28

Met Pro Lys Glu Arg Arg Ser Arg Arg Arg Pro Gln Pro Ile Ile Arg
1 5 10 15

Trp Val Ser Leu Thr Leu Thr Leu Leu Ala Leu Cys Gln Pro Ile Gln
20 25 30

Thr Trp Arg Cys Ser Leu Ser Leu Gly Asn Gln Gln Trp Met Thr Thr
35 40 45

Tyr Asn Gln Glu Ala Lys Phe Phe Ile Ser Ile Asp Gln Ile Leu Glu
50 55 60

Ala His Asn Gln Ser Pro Phe Cys Pro Arg Ser Pro Arg Tyr Thr Leu
65 70 75 80

Asp Phe Val Asn Gly Tyr Pro Lys Ile Tyr Trp Pro Pro Pro Gln Gly
85 90 95

Arg Arg Arg Phe Gly Ala Arg Ala Met Val Thr Tyr Asp Cys Glu Pro
100 105 110

Arg Cys Pro Tyr Val Gly Ala Asp His Phe Asp Cys Pro His Trp Asp
115 120 125

Asn Ala Ser Gln Ala Asp Gln Gly Ser Phe Tyr Val Asn His Gln Thr
130 135 140

Leu Phe Leu His Leu Lys Gln Cys His Gly Ile Phe Thr Leu Thr Trp
145 150 155 160

Glu Ile Trp Gly Tyr Asp Pro Leu Ile Thr Phe Ser Leu His Lys Ile
165 170 175

Pro Ala Pro Pro Gln
180

<210> SEQ ID NO 29
<211> LENGTH: 181
<212> TYPE: PRT
<213> ORGANISM: Artificial Sequence
<220> FEATURE:
<223> OTHER INFORMATION: BLV.RBD

<400> SEQUENCE: 29

```
Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln
            180


<210> SEQ ID NO 30
<211> LENGTH: 215
<212> TYPE: PRT
<213> ORGANISM: Artificial Sequence
<220> FEATURE:
<223> OTHER INFORMATION: BLV.RBD

<400> SEQUENCE: 30

Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175
```

-continued

Pro Ala Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asp Cys Ala Ile Cys
210 215

<210> SEQ ID NO 31
<211> LENGTH: 215
<212> TYPE: PRT
<213> ORGANISM: Artificial Sequence
<220> FEATURE:
<223> OTHER INFORMATION: BLV.RBD

<400> SEQUENCE: 31

Met Pro Lys Glu Arg Arg Ser Arg Arg Arg Pro Gln Pro Ile Ile Arg
1 5 10 15

Trp Val Ser Leu Thr Leu Thr Leu Leu Ala Leu Cys Gln Pro Ile Gln
20 25 30

Thr Trp Arg Cys Ser Leu Ser Leu Gly Asn Gln Gln Trp Met Thr Thr
35 40 45

Tyr Asn Gln Glu Ala Lys Phe Phe Ile Ser Ile Asp Gln Ile Leu Glu
50 55 60

Ala His Asn Gln Ser Pro Phe Cys Pro Arg Ser Pro Arg Tyr Thr Leu
65 70 75 80

Asp Phe Val Asn Gly Tyr Pro Lys Ile Tyr Trp Pro Pro Pro Gln Gly
85 90 95

Arg Arg Arg Phe Gly Ala Arg Ala Met Val Thr Tyr Asp Cys Glu Pro
100 105 110

Arg Cys Pro Tyr Val Gly Ala Asp His Phe Asp Cys Pro His Trp Asp
115 120 125

Asn Ala Ser Gln Ala Asp Gln Gly Ser Phe Tyr Val Asn His Gln Thr
130 135 140

Leu Phe Leu His Leu Lys Gln Cys His Gly Ile Phe Thr Leu Thr Trp
145 150 155 160

Glu Ile Trp Gly Tyr Asp Pro Leu Ile Thr Phe Ser Leu His Lys Ile
165 170 175

Pro Ala Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asp Cys Ala Ile Cys
210 215

<210> SEQ ID NO 32
<211> LENGTH: 215
<212> TYPE: PRT
<213> ORGANISM: Artificial Sequence
<220> FEATURE:
<223> OTHER INFORMATION: BLV.RBD

<400> SEQUENCE: 32

Met Pro Lys Glu Arg Arg Ser Arg Arg Arg Pro Gln Pro Ile Ile Arg
1 5 10 15

Trp Ile Ser Leu Thr Leu Thr Leu Leu Ala Leu Cys Gln Pro Ile Gln
20 25 30

Thr Trp Arg Cys Ser Leu Ser Leu Gly Asn Gln Gln Trp Met Thr Thr
35 40 45

Tyr Asn Gln Glu Ala Lys Phe Phe Ile Ser Ile Asp Gln Ile Leu Glu
50 55 60

Ala His Asn Gln Ser Pro Phe Cys Pro Arg Ser Pro Arg Tyr Thr Leu
65 70 75 80

Asp Phe Val Asn Gly Tyr Pro Lys Ile Tyr Trp Pro Pro Pro Gln Gly
85 90 95

Arg Arg Arg Phe Gly Ala Arg Ala Met Val Thr Tyr Asp Cys Glu Pro
100 105 110

Arg Cys Pro Tyr Val Gly Ala Asp His Phe Asp Cys Pro His Trp Asp
115 120 125

Asn Ala Ser Gln Ala Asp Gln Gly Ser Phe Tyr Val Asn His Gln Thr
130 135 140

Leu Phe Leu His Leu Lys Gln Cys His Gly Ile Phe Thr Leu Thr Trp
145 150 155 160

Glu Ile Trp Gly Tyr Asp Pro Leu Ile Thr Phe Ser Leu His Lys Ile
165 170 175

Pro Asp Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asp Cys Ala Ile Cys
210 215

<210> SEQ ID NO 33
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 33

Met Pro Lys Glu Arg Arg Ser Arg Arg Arg Pro Gln Pro Ile Ile Arg
1 5 10 15

Trp Ile Ser Leu Thr Leu Thr Leu Leu Ala Leu Cys Gln Pro Ile Gln
20 25 30

Thr Trp Arg Cys Ser Leu Ser Leu Gly Asn Gln Gln Trp Met Thr Thr
35 40 45

Tyr Asn Gln Glu Ala Lys Phe Phe Ile Ser Ile Asp Gln Ile Leu Glu
50 55 60

Ala His Asn Gln Ser Pro Phe Cys Pro Arg Ser Pro Arg Tyr Thr Leu
65 70 75 80

Asp Phe Val Asn Gly Tyr Pro Lys Ile Tyr Trp Pro Pro Pro Gln Gly
85 90 95

Arg Arg Arg Phe Gly Ala Arg Ala Met Val Thr Tyr Asp Cys Glu Pro
100 105 110

Arg Cys Pro Tyr Val Gly Ala Asp His Phe Asp Cys Pro His Trp Asp
115 120 125

Asn Ala Ser Gln Ala Asp Gln Gly Ser Phe Tyr Val Asn His Gln Thr
130 135 140

Leu Phe Leu His Leu Lys Gln Cys His Gly Ile Phe Thr Leu Thr Trp
145 150 155 160

Glu Ile Trp Gly Tyr Asp Pro Leu Ile Thr Phe Ser Leu His Lys Ile
165 170 175

Pro Ala Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asp Cys Ala Ile Cys Trp Glu Pro Ser Pro Pro Trp Ala Pro
210 215 220

Glu Ile Leu Val Tyr Asn Lys Thr Ile Ser Ser Ser Gly Pro Gly Leu
225 230 235 240

Ala Leu Pro Asp Ala Gln Ile Phe Trp Val Asn Thr Ser Leu Phe Asn
245 250 255

Thr Thr Gln Gly Trp His His Pro Ser Gln Arg Leu Leu Phe Asn Val
260 265 270

Ser Gln Gly Asn Ala Leu Leu Leu Pro Pro Ile Ser Leu Val Asn Leu
275 280 285

Ser Thr Ala Ser Ser Ala Pro Pro Thr Arg Val Arg Arg Ser Pro Val
290 295 300

Ala Ala Leu Thr Leu Gly Leu Ala Leu Ser Val Gly Leu Thr Gly Ile
305 310 315 320

Asn Val Ala Val Ser Ala Leu Ser His Gln Arg Leu Thr Ser Leu Ile
325 330 335

His Val Leu Glu Gln Asp Gln Gln Arg Leu Ile Thr Ala Ile Asn Gln
340 345 350

Thr His Tyr Asn Leu Leu Asn Val Ala Ser Val Val Ala Gln Asn Arg
355 360 365

Arg Gly Leu Asp Trp Leu Tyr Ile Arg Leu Gly Phe Gln Ser Leu Cys
370 375 380

Pro Thr Ile Asn Glu Pro Cys Cys Phe Leu Arg Ile Gln Asn Asp Ser
385 390 395 400

Ile Ile Arg Leu Gly Asp Leu Gln Pro Leu Ser Gln Arg Val Ser Thr
405 410 415

Asp Trp Gln Trp Pro Trp Asn Trp Asp Leu Gly Leu Thr Ala Trp Val
420 425 430

Arg Glu Thr Ile His Ser Val Leu Ser Leu Phe Leu Leu Ala Leu Phe
435 440 445

Leu Leu Phe Leu Ala Pro Cys Leu Ile Lys Cys Leu Thr Ser Arg Leu
450 455 460

Leu Lys Leu Leu Arg Gln Ala Pro His Phe Pro Glu Ile Ser Phe Pro
465 470 475 480

Pro Lys Pro Asp Ser Asp Tyr Gln Ala Leu Leu Pro Ser Ala Pro Glu
485 490 495

Ile Tyr Ser His Leu Ser Pro Thr Lys Pro Asp Tyr Ile Asn Leu Arg
500 505 510

Pro Cys Pro
515

<210> SEQ ID NO 34
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 34

Met Pro Lys Glu Arg Arg Ser Arg Arg Arg Pro Gln Pro Ile Ile Arg
1 5 10 15

Trp Val Ser Leu Thr Leu Thr Leu Leu Ala Leu Cys Gln Pro Ile Gln
20 25 30

-continued

```
Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445
```

-continued

```
Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515


<210> SEQ ID NO 35
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 35

Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285
```

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515

<210> SEQ ID NO 36
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 36

Met Pro Lys Lys Arg Arg Ser Arg Arg Arg Pro Gln Pro Ile Ile Arg
1               5                   10                  15

Trp Ile Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

-continued

```
Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515
```

<210> SEQ ID NO 37
<211> LENGTH: 515
<212> TYPE: PRT

-continued

<213> ORGANISM: Artificial Sequence
<220> FEATURE:
<223> OTHER INFORMATION: Amino acid sequence of BLV envelope

<400> SEQUENCE: 37

```
Met Pro Lys Lys Arg Arg Ser Arg Arg Arg Pro Gln Pro Ile Ile Arg
1               5                   10                  15

Trp Val Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
```

-continued

```
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515


<210> SEQ ID NO 38
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 38

Met Pro Lys Lys Arg Arg Ser Arg Arg Arg Pro Gln Pro Ile Ile Arg
1               5                   10                  15

Trp Ile Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
```

```
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515


<210> SEQ ID NO 39
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 39

Met Pro Lys Glu Arg Arg Ser Arg Arg Arg Pro Gln Pro Ile Ile Arg
1               5                   10                  15

Trp Ile Ser Leu Thr Leu Thr Leu Leu Ser Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Ser Ile Ala Ile Asp Gln Ile Leu Glu
    50                  55                  60

Ala His Asn Gln Ser Pro Phe Cys Pro Arg Ser Pro Arg Tyr Thr Leu
```

-continued

```
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Asn Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Ala
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Ala
465                 470                 475                 480

Pro Lys Pro Asp Ser Asp Tyr Gln Ala Leu Leu Pro Ser Ala Pro Glu
                485                 490                 495
```

Ile Tyr Ser His Leu Ser Pro Thr Lys Pro Asp Tyr Ile Asn Leu Arg
500 505 510

Pro Cys Pro
515

<210> SEQ ID NO 40
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 40

Met Pro Lys Glu Arg Arg Ser Arg Arg Arg Pro Gln Pro Ile Ile Arg
1 5 10 15

Trp Val Ser Leu Thr Leu Thr Leu Leu Ser Leu Cys Gln Pro Ile Gln
20 25 30

Thr Trp Arg Cys Ser Leu Ser Leu Gly Asn Gln Gln Trp Met Thr Thr
35 40 45

Tyr Asn Gln Glu Ala Lys Phe Ser Ile Ala Ile Asp Gln Ile Leu Glu
50 55 60

Ala His Asn Gln Ser Pro Phe Cys Pro Arg Ser Pro Arg Tyr Thr Leu
65 70 75 80

Asp Phe Val Asn Gly Tyr Pro Lys Ile Tyr Trp Pro Pro Pro Gln Gly
85 90 95

Arg Arg Arg Phe Gly Ala Arg Ala Met Val Thr Tyr Asp Cys Glu Pro
100 105 110

Arg Cys Pro Tyr Val Gly Ala Asp His Phe Asp Cys Pro His Trp Asp
115 120 125

Asn Ala Ser Gln Ala Asp Gln Gly Ser Phe Tyr Val Asn His Gln Ile
130 135 140

Leu Phe Leu His Leu Lys Gln Cys His Gly Ile Phe Thr Leu Thr Trp
145 150 155 160

Glu Ile Trp Gly Tyr Asp Pro Leu Ile Thr Phe Ser Leu His Lys Ile
165 170 175

Pro Ala Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asp Cys Ala Ile Cys Trp Glu Pro Ser Pro Pro Trp Ala Pro
210 215 220

Glu Ile Leu Val Tyr Asn Lys Thr Ile Ser Asn Ser Gly Pro Gly Leu
225 230 235 240

Ala Leu Pro Asp Ala Gln Ile Phe Trp Val Asn Thr Ser Leu Phe Asn
245 250 255

Thr Thr Gln Gly Trp His His Pro Ser Gln Arg Leu Leu Phe Asn Val
260 265 270

Ser Gln Gly Asn Ala Leu Leu Leu Pro Pro Ile Ser Leu Val Asn Leu
275 280 285

Ser Thr Ala Ser Ser Ala Pro Pro Thr Arg Val Arg Arg Ser Pro Ala
290 295 300

Ala Ala Leu Thr Leu Gly Leu Ala Leu Ser Val Gly Leu Thr Gly Ile
305 310 315 320

Asn Val Ala Val Ser Ala Leu Ser His Gln Arg Leu Thr Ser Leu Ile
325 330 335

```
His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Ala
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515


<210> SEQ ID NO 41
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 41

Met Pro Lys Glu Arg Arg Ser Arg Arg Arg Pro Gln Pro Ile Ile Arg
1               5                   10                  15

Trp Ile Ser Leu Thr Leu Thr Leu Leu Ser Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Ser Ile Ala Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175
```

Pro Asp Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asp Cys Ala Ile Cys Trp Glu Pro Ser Pro Pro Trp Ala Pro
210 215 220

Glu Ile Leu Val Tyr Asn Lys Thr Ile Ser Asn Ser Gly Pro Gly Leu
225 230 235 240

Ala Leu Pro Asp Ala Gln Ile Phe Trp Val Asn Thr Ser Leu Phe Asn
245 250 255

Thr Thr Gln Gly Trp His His Pro Ser Gln Arg Leu Leu Phe Asn Val
260 265 270

Ser Gln Gly Asn Ala Leu Leu Leu Pro Pro Ile Ser Leu Val Asn Leu
275 280 285

Ser Thr Ala Ser Ser Ala Pro Pro Thr Arg Val Arg Arg Ser Pro Ala
290 295 300

Ala Ala Leu Thr Leu Gly Leu Ala Leu Ser Val Gly Leu Thr Gly Ile
305 310 315 320

Asn Val Ala Val Ser Ala Leu Ser His Gln Arg Leu Thr Ser Leu Ile
325 330 335

His Val Leu Glu Gln Asp Gln Gln Arg Leu Ile Thr Ala Ile Asn Gln
340 345 350

Thr His Tyr Asn Leu Leu Asn Val Ala Ser Val Val Ala Gln Asn Arg
355 360 365

Arg Gly Leu Asp Trp Leu Tyr Ile Arg Leu Gly Phe Gln Ser Leu Cys
370 375 380

Pro Thr Ile Asn Glu Pro Cys Cys Phe Leu Arg Ile Gln Asn Asp Ser
385 390 395 400

Ile Ile Arg Leu Gly Asp Leu Gln Pro Leu Ser Gln Arg Val Ser Thr
405 410 415

Asp Trp Gln Trp Pro Trp Asn Trp Asp Leu Gly Leu Thr Ala Trp Val
420 425 430

Arg Glu Thr Ile His Ser Val Leu Ser Leu Phe Leu Leu Ala Leu Phe
435 440 445

Leu Leu Phe Leu Ala Pro Cys Leu Ile Lys Cys Leu Thr Ser Arg Leu
450 455 460

Leu Lys Leu Leu Arg Gln Ala Pro His Phe Pro Glu Ile Ser Leu Ala
465 470 475 480

Pro Lys Pro Asp Ser Asp Tyr Gln Ala Leu Leu Pro Ser Ala Pro Glu
485 490 495

Ile Tyr Ser His Leu Ser Pro Thr Lys Pro Asp Tyr Ile Asn Leu Arg
500 505 510

Pro Cys Pro
515

<210> SEQ ID NO 42
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 42

Met Pro Lys Glu Arg Arg Ser Arg Arg Arg Pro Gln Pro Ile Ile Arg
1 5 10 15

-continued

```
Trp Ile Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Lys Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430
```

```
Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515


<210> SEQ ID NO 43
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 43

Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Lys Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270
```

-continued

```
Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515


<210> SEQ ID NO 44
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 44

Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Arg Pro Ile Gln
            20                  25                  30

Thr Trp Arg Cys Ser Leu Ser Leu Gly Asn Gln Gln Trp Met Thr Ala
        35                  40                  45

Tyr Asn Gln Glu Ala Lys Phe Ser Ile Ser Ile Asp Gln Ile Leu Glu
    50                  55                  60

Ala His Asn Gln Ser Pro Phe Cys Ala Lys Ser Pro Arg Tyr Thr Leu
65                  70                  75                  80

Asp Ser Val Asn Gly Tyr Pro Lys Ile Tyr Trp Pro Pro Pro Lys Gly
                85                  90                  95

Arg Arg Arg Phe Gly Ala Arg Ala Met Val Thr Tyr Asp Cys Glu Pro
            100                 105                 110
```

-continued

```
Arg Cys Pro Tyr Val Gly Ala Asp Arg Phe Asp Cys Pro His Trp Asp
        115                 120                 125

Asn Ala Ser Gln Ala Asp Gln Gly Ser Phe Tyr Val Asn His Gln Ile
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asp Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Ser Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Thr Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Leu Thr
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Val Lys Pro Asp Tyr Ile Asn Leu Arg
            500                 505                 510

Pro Cys Pro
        515
```

<210> SEQ ID NO 45
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 45

```
Met Pro Lys Glu Arg Arg Ser Arg Arg Arg Pro Gln Pro Ile Ile Arg
1               5                   10                  15

Trp Ile Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asn Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
```

```
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Leu Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515
```

<210> SEQ ID NO 46
<211> LENGTH: 1548
<212> TYPE: DNA
<213> ORGANISM: Artificial Sequence
<220> FEATURE:
<223> OTHER INFORMATION: Nucleic acid sequence of BLV envelope

<400> SEQUENCE: 46

```
atgcccaaag aacgacggtc ccgaagacgc ccacaaccga tcatcagatg gatctccctc     60

actcttactc tcctcgctct ctgtcagccc atccagactt ggagatgctc cctgtcccta    120

ggaaatcaac aatggatgac aacatataac caagaggcaa aatttttcat ctccattgac    180

caaatactag aggctcataa tcaatcacct ttctgtccca ggtctcccag atacaccttg    240

gactttgtaa atggttatcc taagatctat tggccccccc cacaagggcg gcgccggttt    300

ggagccaggg ccatggtcac atatgattgc gagccccgat gcccttatgt gggggcagat    360

cacttcgact gcccccactg ggacaatgcc tcccaggccg atcaaggatc cttttatgtc    420

aatcatcaga ctttattcct gcatctcaaa caatgtcatg gaattttcac tctaacctgg    480

gaaatatggg gatatgatcc cctgatcacc ttttctttac ataaaatccc tgatccccct    540

caacccgact tccctcagct gaacagtgac tgggttccct ctgtcagatc atgggccctg    600

cttttaaatc aaacggcacg ggccttccca aactgtgcta tatgttggga accctcccct    660

ccctgggctc ccgaaatatt agtatataac aaaaccatct ccagctctgg acccggtctc    720

gccctcccgg acgcccaaat cttctgggtc aacacgtcct tgtttaacac cacccaagga    780

tggcaccacc cttcccagag gttgttgttc aacgtttctc aaggcaacgc cttattattg    840

ccccctatct ccctggttaa tctctctacg gcttcctccg cccctcctac ccgggtcaga    900

cgcagtcccg tcgcagccct gaccttaggc ctagccctgt cagtggggct cactggaatt    960

aatgtagccg tgtctgccct tagccatcag agactcacct ccctgatcca cgttctggag   1020

caagatcagc aacgcttgat cacagcaatt aaccagaccc actataattt gcttaatgtg   1080

gcctctgtgg tcgcccagaa ccgacggggg cttgattggt tgtacatccg gctgggtttt   1140

caaagtctat gtcccacaat caatgaacct tgctgtttcc tgcgcatcca aaatgactcc   1200
```

attatccgcc tcggtgatct ccagcctctc tcgcaaagag tctctacaga ctggcagtgg 1260
ccctggaatt gggatctggg gctcaccgcc tgggtgcggg agctcattca ttctgttcta 1320
agcctattcc tattagccct ttttttgctc ttcttggccc cctgcctgat aaaatgcttg 1380
acctctcgcc ttttaaaact cctccggcag gctccccact tccctgaaat ctccttcccc 1440
cctaaacccg attctgatta tcaggccttg ctaccatccg cgccagagat ctactctcac 1500
ctctccccca ccaaacccga ttacatcaac cttcgaccct gcccctag 1548

<210> SEQ ID NO 47
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 47

Met Pro Lys Glu Arg Arg Ser Arg Arg Arg Pro Gln Pro Ile Ile Arg
1 5 10 15

Trp Ile Ser Leu Thr Leu Thr Leu Leu Ala Leu Cys Gln Pro Ile Gln
20 25 30

Thr Trp Arg Cys Ser Leu Ser Leu Gly Asn Gln Gln Trp Met Thr Thr
35 40 45

Tyr Asn Gln Glu Ala Lys Phe Phe Ile Ser Ile Asp Gln Ile Leu Glu
50 55 60

Ala His Asn Gln Ser Pro Phe Cys Pro Arg Ser Pro Arg Tyr Thr Leu
65 70 75 80

Asp Phe Val Asn Gly Tyr Pro Lys Ile Tyr Trp Pro Pro Pro Gln Gly
85 90 95

Arg Arg Arg Phe Gly Ala Arg Ala Met Val Thr Tyr Asp Cys Glu Pro
100 105 110

Arg Cys Pro Tyr Val Gly Ala Asp His Phe Asp Cys Pro His Trp Asp
115 120 125

Asn Ala Ser Gln Ala Asp Gln Gly Ser Phe Tyr Val Asn His Gln Thr
130 135 140

Leu Phe Leu His Leu Lys Gln Cys His Gly Ile Phe Thr Leu Thr Trp
145 150 155 160

Glu Ile Trp Gly Tyr Asp Pro Leu Ile Thr Phe Ser Leu His Lys Ile
165 170 175

Pro Ala Pro Pro Gln Pro Asp Phe Pro Gln Leu Asn Ser Asp Trp Val
180 185 190

Pro Ser Val Arg Ser Trp Ala Leu Leu Leu Asn Gln Thr Ala Arg Ala
195 200 205

Phe Pro Asn Cys Ala Ile Cys Trp Glu Pro Ser Pro Pro Trp Ala Pro
210 215 220

Glu Ile Leu Val Tyr Asn Lys Thr Ile Ser Ser Ser Gly Pro Gly Leu
225 230 235 240

Ala Leu Pro Asp Ala Gln Ile Phe Trp Val Asn Thr Ser Leu Phe Asn
245 250 255

Thr Thr Gln Gly Trp His His Pro Ser Gln Arg Leu Leu Phe Asn Val
260 265 270

Ser Gln Gly Asn Ala Leu Leu Leu Pro Pro Ile Ser Leu Val Asn Leu
275 280 285

Ser Thr Ala Ser Ser Ala Pro Pro Thr Arg Val Arg Arg Ser Pro Val
290 295 300

```
Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Leu Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515
```

<210> SEQ ID NO 48
<211> LENGTH: 515
<212> TYPE: PRT
<213> ORGANISM: Artificial Sequence
<220> FEATURE:
<223> OTHER INFORMATION: Amino acid sequence of BLV envelope

<400> SEQUENCE: 48

```
Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140
```

-continued

```
Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Ala Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asn Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
                405                 410                 415

Asp Trp Gln Trp Pro Trp Asn Trp Asp Leu Gly Leu Thr Ala Trp Val
            420                 425                 430

Arg Glu Leu Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515


<210> SEQ ID NO 49
<211> LENGTH: 515
<212> TYPE: PRT
<213> ORGANISM: Artificial Sequence
<220> FEATURE:
<223> OTHER INFORMATION: Amino acid sequence of BLV envelope
```

-continued

<400> SEQUENCE: 49

```
Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Pro Gln Gly
                85                  90                  95

Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
        115                 120                 125

Asn Ala Ser Gln Ala Asp Gln Gly Ser Phe Tyr Val Asn His Gln Thr
    130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
        195                 200                 205

Phe Pro Asn Cys Ala Ile Cys Trp Glu Pro Ser Pro Pro Trp Ala Pro
    210                 215                 220

Glu Ile Leu Val Tyr Asn Lys Thr Ile Ser Ser Ser Gly Pro Gly Leu
225                 230                 235                 240

Ala Leu Pro Asp Ala Gln Ile Phe Trp Val Asn Thr Ser Leu Phe Asn
                245                 250                 255

Thr Thr Gln Gly Trp His His Pro Ser Gln Arg Leu Leu Phe Asn Val
            260                 265                 270

Ser Gln Gly Asn Ala Leu Leu Leu Pro Pro Ile Ser Leu Val Asn Leu
        275                 280                 285

Ser Thr Ala Ser Ser Ala Pro Pro Thr Arg Val Arg Arg Ser Pro Val
    290                 295                 300

Ala Ala Leu Thr Leu Gly Leu Ala Leu Ser Val Gly Leu Thr Gly Ile
305                 310                 315                 320

Asn Val Ala Val Ser Ala Leu Ser His Gln Arg Leu Thr Ser Leu Ile
                325                 330                 335

His Val Leu Glu Gln Asp Gln Gln Arg Leu Ile Thr Ala Ile Asn Gln
            340                 345                 350

Thr His Tyr Asn Leu Leu Asn Val Ala Ser Val Val Ala Gln Asn Arg
        355                 360                 365

Arg Gly Leu Asp Trp Leu Tyr Ile Arg Leu Gly Phe Gln Ser Leu Cys
    370                 375                 380

Pro Thr Ile Asn Glu Pro Cys Cys Phe Leu Arg Ile Gln Asn Asp Ser
385                 390                 395                 400

Ile Ile Arg Leu Gly Asp Leu Gln Pro Leu Ser Gln Arg Val Ser Thr
```

-continued

```
                405                 410                 415

Asp Trp Gln Trp Pro Trp Asn Trp Asp Leu Gly Leu Thr Ala Trp Val
            420                 425                 430

Arg Glu Leu Ile His Ser Val Leu Ser Leu Phe Leu Leu Ala Leu Phe
        435                 440                 445

Leu Leu Phe Leu Ala Pro Cys Leu Ile Lys Cys Leu Thr Ser Arg Leu
    450                 455                 460

Leu Lys Leu Leu Arg Gln Ala Pro His Phe Pro Glu Ile Ser Phe Pro
465                 470                 475                 480

Pro Lys Pro Asp Ser Asp Tyr Gln Ala Leu Leu Pro Ser Ala Pro Glu
                485                 490                 495

Ile Tyr Ser His Leu Ser Pro Thr Lys Pro Asp Tyr Ile Asn Leu Arg
            500                 505                 510

Pro Cys Pro
        515
```

USE OF RECEPTOR-BINDING DOMAIN DERIVED FROM BOVINE LEUKEMIA VIRUS FOR THE DIAGNOSIS OR TREATMENT OF CATIONIC L-AMINO ACID TRANSPORTER-RELATED DISEASES

FIELD OF INVENTION

The present invention relates to the diagnosis or treatment of a cationic L-amino acid transporter-related disease, such as, for example, a CAT1-related disease. In particular, the present invention relates to methods comprising the detection of the binding of the cationic amino acid transporter CAT1/SLC7A1 with a receptor-binding domain (RBD) derived from the bovine leukemia virus (BIN) envelope glycoprotein.

BACKGROUND OF INVENTION

Arginine, lysine, histidine and ornithine are amino acids involved in diverse metabolic pathways. These pathways control the metabolism of fatty acids, glucose, amino acids and proteins but they are also involved in transport, processing and excretion of nitrogen, urea synthesis, and creatine and nitric oxide synthesis.

The dysregulation of one of these pathways is one of the hallmarks of diverse diseases such as cancer (including in particular carcinoma, sarcoma, and leukemia), diabetes, obesity, cardiovascular and inflammatory diseases that are characterized by an increased or decreased uptake of arginine, lysine, histidine and ornithine in cells, tissues or organs affected by such dysregulation. Therefore, there is growing interest in targeting pathways related to these amino acids. For instance, there have been many types of cancer characterized by a dysregulation of arginine-related pathways. Arginine deprivation has been one of the strategies to fight against these cancers. However, resistance to these treatments appeared besides undesirable side effects (Feun et al., 2015. Curr. Opin. Nuir. Metab. Care. 13(1):78-82; Qiu et al., 2015. Cancer Lett. 364(1): 1-7), therefore there is a need to develop new strategies and alternative therapies.

The state of the art teaches that the cationic L-amino acid transporter CAT1 is the main transporter for arginine (Gloss et al., 2004. J. Nutr. 134(10 Suppl): 2752S-2759S) or for lysine, histidine and ornithine influx. So far, the Murine type C ecotropic retrovirus envelope glycoprotein is well known for its binding to mouse or rat CAT1 (Albritton et al., 1993. J. Viral. 67(4):2091-2096). However, there is a lack of accurate ligand targeting other mammalian CAT1, in particular human, cattle and flock CAT1.

The inventors discovered that a ligand derived from the bovine leukemia virus (BLV) envelope glycoprotein bound specifically to CAT1 of different mammals including humans. Surprisingly, the inventors demonstrate that this ligand blocks arginine influx within cells, thereby preventing arginine accumulation within these cells.

The present invention thus relates to the use of a BLV-RBD for the diagnosis or treatment of CAT1-related diseases.

SUMMARY

The present invention thus relates to an in vitro method for detecting and/or quantifying the cationic amino acid transporter-1 (CAT1) in a cell, wherein said method comprises:

a. contacting said cell with at least one bovine leukemia virus (BLV)-RBD ligand, a variant and/or a fragment thereof, and
b. determining and/or quantifying the binding of said at least one ligand variant and/or fragment thereof to CAT1.

In one embodiment, said method further comprises comparing the binding level determined and/or quantified at step b with a reference value.

In one embodiment, said method is for diagnosing or monitoring a CAT1-related disease or a BLV infection in a subject.

In one embodiment, said at least one bovine leukemia virus (BLV)-RBD ligand, variant and/or fragment thereof is selected from the group comprising SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 and 49, variants and fragments thereof.

The present invention further relates to a diagnostic composition comprising at least one BLV-RBD ligand, a variant and/or a fragment thereof coupled with at least one contrast agent, and a pharmaceutically acceptable excipient.

The present invention further relates to a BLV-RBD ligand, a variant and/or a fragment thereof, for use in the in vivo diagnosis of a CAT1-related disease, preferably by medical imaging.

The present invention further relates to a BLV-RBD ligand, a variant and/or a fragment thereof, for use in the treatment of a CAT1-related disease.

In one embodiment, said CAT1-related disease is selected from the group comprising arginine-related diseases, lysine-related diseases, histidine-related diseases, omithine-related diseases, and inflammatory diseases.

Another object of the invention is a BLV-RBD ligand, a variant and/or a fragment thereof, for use in the treatment of a BLV infection.

Another object of the invention is a pharmaceutical composition comprising at least one BLV-RBD ligand, a variant and/or a fragment thereof for use as described hereinabove, and a pharmaceutically acceptable excipient.

The present invention further relates to a medicament comprising at least one BLV-RBD ligand, a variant and/or a fragment thereof for use as described hereinabove.

In one embodiment, the BLV-RBD ligand comprises SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 and/or 49, a variant and/or a fragment thereof.

Definitions

In the present invention, the following terms have the following meanings:

The term "cell surface nutrient transporter" refers to the nutrient transporter CAT1. CAT1 may be anchored in the plasma membrane of a cell or within a cell.

"CAT1/SLC7A1" refers to a cationic L-amino acid transporter. CAT1 mediates sodium-independent and pH-insensitive transport of amino acids that include arginine, ornithine, lysine and histidine. CAT1 is ubiquitously expressed although it is thought to not be present on liver cells and lacrimal gland cells. CAT1 is herein identified as a specific receptor for BLV-RBD. In one embodiment, CAT1 is human CAT1 (accession number: AIC49738, SEQ ID NO: 1), encoded by SEQ ID NO: 2 (accession number: KJ892152). In one embodiment, CAT1 comprises or consists of an amino acid sequence presenting a sequence identity of at least 70% with SEQ ID NO: 1, preferably a sequence identity of at least 75, 80, 85, 90, 91, 92, 93, 94, 95, 96, 97, 98, 99% or more with SEQ ID NO: 1. In one embodiment, CAT1 is encoded by a nucleotide sequence presenting a sequence identity of at least 70% with SEQ ID NO: 2, preferably a sequence identity of at least 75, 80, 85, 90, 91, 92, 93, 94, 95, 96, 97, 98, 99% or more with SEQ ID NO: 2. In one embodiment, CAT1 comprises or consists of a fragment of SEQ ID NO: 1, preferably a fragment of at least about 100 amino acids, more preferably of at least about 150, 200, 250, 300, 350, 400, 450, 500, 550, 600 amino acids. In one embodiment, CAT1 is not mouse CAT1 (accession number: Q09143, SEQ ID NO: 23). In one embodiment, CAT is not rat CAT1 (accession number: P30823, SEQ ID NO: 24).

The term "diagnostic composition" refers to a composition to be administered in a subject in order to perform a diagnosis and in particular an in vivo diagnosis. In one embodiment, a diagnostic composition is for detecting cells wherein the function of a cationic L-amino acid transporter, preferably of CAT1, is dysregulated, preferably within the body of a subject. In another embodiment, the present invention relates to a diagnostic composition for detecting cells which are infected or not yet infected by BLV, preferably within the body of a subject.

The term "effective amount" refers to the level or amount of a ligand, preferably of the at least one BLV-RBD ligand that is aimed at binding to CAT1, without causing significant negative or adverse side effects to the subject wherein the function of a cationic L-amino acid transporter, preferably of CAT1, is dysregulated; or to the subject infected by BLV.

The term "therapeutically effective amount" means level or amount of agent that is aimed at, without causing significant negative or adverse side effects to the target, (1) delaying or preventing the onset of a CAT1-related disease or a BLV infection: (2) slowing down or stopping the progression, aggravation, or deterioration of one or more symptoms of a CAT1-related disease or a BLV infection; (3) bringing about ameliorations of the symptoms of a CAT1-related disease or a BLV infection; (4) reducing the seventy or incidence of a CAT1-related disease or a BLV infection; or (5) curing a CAT1-related disease or a BLV infection. A therapeutically effective amount may be administered prior to the onset of a CAT1-related disease or a BLV infection, for a prophylactic or preventive action. Alternatively or additionally, the therapeutically effective amount may be administered after initiation of a CAT1-related disease or a BLV infection, for a therapeutic action.

The term "treatment" refers to both therapeutic treatment and prophylactic or preventative measures; wherein the object is to prevent or slow down (lessen) a CAT1-related disease or a BLV infection. Those in need of treatment include those already with a CAT1-related disease or a BLV infection as well as those prone to have a CAT1-related disease or a BLV infection or those in whom a CAT1-related disease or a BIN infection is to be prevented. A subject or mammal is successfully "treated" for a disease if, after receiving a therapeutic amount of a ligand according to the invention, the patient shows observable and/or measurable reduction in or absence of one or more of the following: reduction in the number of pathogenic cells; reduction in the percent of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

The term "polypeptide" refers to a linear polymer of amino acids (preferably at least 50 amino acids) linked together by peptide bonds.

The term "protein" specifically refers to a functional entity formed of one or more polypeptides, and optionally of non-poly peptides cofactors.

The term "identity", when used in a relationship between the sequences of two or more polypeptides or of two or more DNA sequences, refers to the degree of sequence relatedness between polypeptides or DNA sequences (respectively), as determined by the number of matches between strings of two or more amino acid residues or of two or more nucleotides, respectively. "Identity" measures the percent of identical matches between the smaller of two or more sequences with gap alignments (if any) addressed by a particular mathematical model or computer program (i.e., "algorithms"). Identity of related polypeptides or DNA sequences can be readily calculated by known methods. Such methods include, but are not limited to, those described in Arthur M. Lesk, Computational Molecular Biology: Sources and Methods for Sequence Analysis (New-York: Oxford University Press, 1988); Douglas W. Smith, Biocomputing: Informatics and Genome Projects (New-York: Academic Press, 1993); Hugh G. Griffin and Annette M. Griffin, Computer Analysis of Sequence Data, Part 1 (New Jersey: Humana Press, 1994); Gunnar von Heinje, Sequence Analysis in Molecular Biology: Treasure Trove or Trivial Pursuit (Academic Press, 1987); Michael Gribskov and John Devereux, Sequence Analysis Primer (New York: M. Stockton Press, 1991); and Carillo et al., 1988. RAM Appl. Math. 48(5):1073-1082. Preferred methods for determining identity are designed to give the largest match between the sequences tested. Methods of determining identity are described in publicly available computer programs. Preferred computer program methods for determining identity between two sequences include the GCG program package, including GAP (Devereux et al., 1984. Nucl. Acid. Res. 12(1 Pt 1):387-395; Genetics Computer Group, University of Wisconsin Biotechnology Center, Madison, Wis.), BLASTP, BLASTN, TBLASTN and FASTA (Altschul et al., 1990. J Mol. Biol. 215(3):403-410). The BLASTX program is publicly available from the National Center for Biotechnology information (NCBI) and other sources (BLAST Manual, Altschul et al. NCB/NLM/NIH Bethesda, Md. 20894; Altschul et al., 1990. J. Mol. Biol. 215(3):403-

410). The well-known Smith Waterman algorithm may also be used to determine identity.

The term "subject" refers to a mammal, preferably a human, cattle (e.g. cow, bull, calf; heifer), flock, ovine (e.g. sheep, lamb, ewe), caprine (goat, billy goat, kid goat), more preferably a human or a bovine. In one embodiment, a subject may be a "patient", i.e. a mammal, a warm-blooded animal, more preferably a human or a bovine, who/which is awaiting the receipt of, or is receiving medical care or was/is/will be the object of a medical procedure, or is monitored for the development of a disease.

"About" preceding a figure means plus or less 10% of the value of said figure.

DETAILED DESCRIPTION

The present invention relates to an in vitro or in vivo method for detecting and/or quantifying the cell surface nutrient transporter CAT1 in a cell, wherein said method comprises:

a. contacting said cell with at least one ligand, preferably at least one bovine leukemia virus (BLV)-RBD ligand, or a variant and/or a fragment thereof, and b. determining and/or quantifying the binding of said at least one ligand, variant and/or fragment thereof to CAT1.

In one embodiment, the method of the invention comprises a step of comparing the binding determined and/or quantified at step b. with a reference binding value.

As used herein, the term "CAT1 present in a cell" may refer to CAT1 present at the surface of a cell or within the cell.

In one embodiment, the method of the invention is for assessing the expression level of CAT1 present on the cell surface. In another embodiment, the method of the invention is for assessing the expression level of CAT1 present within the cell.

In one embodiment, the method of the invention is for detecting and/or quantifying CAT1 in a sample.

In one embodiment, the sample was obtained from a subject prior to the implementation of the method of the invention. In one embodiment, the method of the invention does not comprise obtaining a sample from the subject, i.e., the method of the invention is non-invasive.

In one embodiment, the sample obtained from the subject to carry out the method of the invention is a biological sample.

In one embodiment, said biological sample is a body fluid sample. Examples of body fluids include, without being limited to, blood, plasma, serum, lymph, urine, cerebrospinal fluid or sweat.

In another embodiment, said biological sample is a cell sample. Examples of cell samples include, without being limited to, peripheral blood mononuclear cells (PBMC), peripheral white blood cells, cell samples obtained from tissue biopsies such as lymph nodes biopsies, intestinal or synovial biopsies, or cell sample obtained from broncho-alveolar lavage or cerebrospinal fluid.

In another embodiment, said biological sample is a tissue sample. Examples of tissue sample include, but are not limited to, biopsy samples.

In one embodiment, the sample obtained from the subject to carry out the method of the invention is a blood sample. In one embodiment, the sample obtained from the subject to carry out the method of the invention is a whole blood sample or a plasma sample.

In one embodiment, the method of the invention is not for detecting and/or quantifying CAT1 in a granulocyte. By "granulocyte" is meant a cell belonging to myelocyte or monocyte lines, such as neutrophils, eosinophils, basophils and mast cells.

In vitro methods for determining and/or quantifying a protein level in a sample are well-known in the art. Examples of such methods include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In vivo methods for determining and/or quantifying a protein level are well-known in the art. Examples of such methods include, but are not limited to, computed tomography (CT scan), endoscopic ultrasound (EUS), magnetic resonance imaging (MRI), positron-emission tomography (PET), single photon emission tomography (SPECT), magnetic resonance cholangiopancreatography, fluorimetry, fluorescence, and near-infrared (NIR) fluorescent imaging.

Methods for analyzing the presence of a protein on the cell surface or within a cell, sample, tissue or organ are well-known to the skilled artisan and include, without limitation, FACS analysis, immunohistochemistry, western blot associated with cell fractionation, enzyme-linked immunosorbent assay (ELISA), sandwich ELISA, fluorescent-linked immunosorbent assay (FLISA), enzyme immunoassay (EIA), radioimmunoassay (RIA), image analysis, for example high content analysis, computed tomography (CT scan), endoscopic ultrasound (EUS), magnetic resonance imaging (MRI), positron-emission tomography (PET), single photon emission tomography (SPECT), magnetic resonance cholangiopancreatography, fluorimetry, fluorescence, and near-infrared (NIR) fluorescent imaging and the like.

In one embodiment, in order to detect the protein on the cell surface, or within a cell, sample, tissue or organ, a step of fixation of said cell, sample, tissue or organ may be required before implementing one of the methods listed hereinabove. Technics for cell, sample, tissue or organ fixation are well known to the skilled artisan and include without limitation, perfusion, immersion with formaldehyde, or methanol/ethanol.

Methods for analyzing the presence of a protein on the cell surface are well-known to the skilled artisan and include, without limitation, FACS analysis, imaging flow cytometry (e.g. AMNIS), immunohistochemistry, western blot associated with cell fractionation, enzyme-linked immunosorbent assay (ELISA), sandwich ELISA, fluorescent-linked immunosorbent assay (FLISA), enzyme immunoassay (EIA), radioimmunoassay (RIA), image analysis, for example high content analysis, computed tomography (CT scan), endoscopic ultrasound (EUS), magnetic resonance imaging (MRI), positron-emission tomography (PET), single photon emission tomography (SPECT), fluorimeter, fluorescence, and near-infrared (NIR) fluorescent imaging and the like.

The expression "determining and/or quantifying the binding" of the at least one ligand (preferably the at least one BLV-RBD ligand), variant and/or fragment thereof means that when the cell surface nutrient transporter CAT1 is present, a complex is formed between CAT1 and the ligand of the invention, variant and/or fragment thereof, that may be detected and optionally quantified.

In one embodiment, the complex can be detected if the ligand, variant and/or fragment thereof has been for example, but not limited to, covalently coupled with a detectable molecule such as an antibody constant fragment (Fc) or a fluorescent compound (e.g. Cyanine dye, Alexa dye, Quantum dye, etc.). The complex can also be detected if the ligand has been tagged with different means well known to the person skilled in the art. For example, but without limitation, a tag used in the invention can be a tag selected from the group comprising or consisting of Hemagglutinin tag, Poly Arginine tag, Poly Histidine tag, Myc tag, Strep tag, S-tag, HAT tag, 3× Flag tag. Calmodulin-Binding Peptide tag, SBP tag, Chitin Binding Domain tag, GST tag, Maltose-Binding Protein tag, Fluorescent Protein tag, T7 tag, V5 tag and X-press tag. These protein tags can be located N-terminally, C-terminally and/or internally of the BLV-RBD ligand of the invention.

The use of the ligand therefore allows on the one hand the identification and detection, and on the other hand the quantification of the complex formed. In one embodiment, detecting and/or quantifying binding is conducted by flow cytometry, immunofluorescence or image analysis, for example high content analysis.

In another embodiment, that complex can be detected if the ligand has been for example, but not limited to, covalently coupled with at least one contrast agent. In one embodiment, detecting and/or quantifying binding is conducted by medical imaging technics.

As used herein, the term "contrast agent" refers to agents used to improve the visibility of internal bodily structures in medical imaging technics, including, but not limited to, magnetic resonance imaging (MRI), X-ray-based imaging techniques such as computed tomography (CT), radiography, endoscopic ultrasound (EUS), positron-emission tomography (PET), single photon emission tomography (SPECT), fluoroscopy, fluorimetry, fluorescence, and near-infrared (NIR) fluorescent imaging.

In one embodiment, the ligand is coupled with at one least contrast agent, wherein said contrast agent may be a radiolabeled agent or a fluorescent agent.

In one embodiment, the radiolabeled agent of the invention is selected from the group comprising a non-metallic radioisotope, non-metallic or metallic dye, paramagnetic metal, or radioactive metal.

Examples of non-metallic radioisotopes comprise, but are not limited to, 1-125, 1-123, 1-131, C-11, F-18, Br-75, Br-76, Br-77, Br-80, and At-211. The non-metallic radioisotopes may be conjugated covalently to either terminus of the ligand, functional groups of amino acid side chains, be part of a linear stabilized peptide as an additional substituent, e.g. in an amino acid phenylalanine or tyrosine carrying fluorine, bromine or iodine, or as an additional substituent carboxy or methyl, or as a replacement of any regular carbon atom in the ligand. Preferably, the ligand is coupled with I-125. These radioisotopes are useful in ligands as positron emission tomography (PET) probes or as single-photon emission computed tomography (SPECT) probes.

Examples of non-metallic or metallic dyes comprise, but are not limited to, organic molecules, e.g., commercial Alexa Fluor®) dyes, fluorescein, rhodamine, or Cy® dyes (such as Cy3, Cy3.5, Cy5, Cy5.5, Cy7, and Cy7.5), complexes of transition metals, e.g. chelates of $Eu^{3+}$, $Tb^{3+}$, or nanoparticles (quantum dots) which adsorb and/or emit light in the visible range or in the near infrared. Organic dyes and chelating systems will be coupled to the ligands as described above for chelators. Conjugation of the ligands with quantum dots is done by procedures known to those skilled in the art. These ligands carrying dyes are useful as optical imaging probes.

Examples of paramagnetic metals comprise, but are not limited to, Gd, Fe, Mn. The metals are attached to the ligands. These ligands are useful as magnetic resonance imaging (MRI) probes.

Examples of radioactive metals comprise, but are not limited to, Cu-64, Cu-67, Ga-67, Ga-68, Zr-89, Y-90, Tc-99m, in-111, Tb-161, Lu-177, Re-186, Re-188, and Bi-213. The radioactive metals (and the paramagnetic metals mentioned above) are attached to the ligands of the invention through chelators as listed above, directly connected to the ligands or through a spacer.

Examples of fluorescent agents include, but are not limited to, GFP, mPlum[g], mCherry[g], tdTomato[g], mStrawberry[g], J-Red, DS-Red monomer[h], mOrange[g], mKO, mCitrine[i], Venus, YPet[g], EYFP, Emerald[g], EGFP, CyPet, mCFP[m], Cerulean[g], T-Sapphire[g], indocyanine green, ZW800-1, Cy5.5 and IRDye800CW.

In one embodiment, the contrast agent is 1-125.

Typical ligands include, but are not limited to, polypeptides and proteins.

In one embodiment, the ligand is an antibody specific to CAT1, and the method of the invention comprises detecting and/or quantifying a complex formed between said antibody and CAT1.

Consequently, in one embodiment, the present invention relates to an in vitro or in vivo method for detecting and/or quantifying the cell surface nutrient transporter CAT1 present in a cell, wherein said method comprises:

a. contacting said cell with at least one antibody specific to CAT1, and
b. determining and/or quantifying the binding of said at least one antibody to CAT1.

In one embodiment, the method of the invention comprises a step of comparing the binding determined and/or quantified at step b. with a reference binding value.

In one embodiment, the ligand is a receptor-binding domain (RBD) ligand and the method of the invention comprises detecting and/or quantifying a complex formed between said RBD ligand and CAT1.

In one aspect of the invention, the ligand is a receptor-binding domain (RBD) ligand, preferably a BLV-RBI) ligand, wherein said RBD ligand comprises a part or the totality of a receptor-binding domain (RBD) derived from the soluble part of the glycoprotein of an enveloped virus that interacts with CAT1.

The expression "that interacts with CAT1" means that the glycoprotein is liable to recognize the CAT1 receptor present in the cell. In one embodiment, a ligand that interacts with CAT1 will thus form a complex with CAT1, which complex may be detected by a method as here above described.

The expression "derived from the soluble part of the glycoprotein of an enveloped virus" means that the ligand is a fragment or a part of a glycoprotein contained in the envelope of a virus and can be obtained, for example, by cloning.

The term "glycoprotein" is to be understood as meaning an envelope glycoprotein, a coat glycoprotein or a fusion glycoprotein, wherein the term "glycoprotein" refers to a protein containing oligosaccharide chains covalently attached to polypeptide side-chains.

RBDs are found, in particular, in glycoproteins of the envelope of viruses, therefore, the receptor-binding domain ligand contains the total RBD or a fragment or part of the RBD.

In one embodiment, the ligand of the invention comprises the cell surface (SU) domain of the glycoprotein envelope of a virus or a fragment of the SU domain, such as, for example, the BLV-RBD. In another embodiment, the ligand of the invention does not comprise the transmembrane (TM) domain of the glycoprotein envelope of a virus. Therefore, in one embodiment of the invention, the ligand of the invention is a soluble peptide, in particular a soluble BLV-RBD. As used herein, the term "soluble peptide" refers to a peptide which is not anchored within a membrane, such as, for example, by a transmembrane or a GPI anchor domain.

In one embodiment, the RBD ligand is not derived from the soluble part of the glycoprotein of Murine type C ecotropic retrovirus. In one embodiment, the RBD ligand is not derived from the soluble part of the glycoprotein of Moloney murine leukemia virus, isolate Shinnick (accession number: P03385, SEQ ID NO: 25). In one embodiment, the RBD ligand is not derived from the soluble part of the glycoprotein of Friend murine leukemia virus, strain 57 (accession number: P03390, SEQ ID NO: 26).

In one embodiment, the RBD ligand is derived from the soluble part of the glycoprotein of a deltaretrovirus.

The deltaretrovirus genus includes viruses that infect humans, various simian species and cattle. Deltaretroviruses include, but are not limited to. Bovine Leukemia Virus (BLV), Human T-cell Leukaemia Viruses 1 to 4 (HTLV1-4), and Simian T-cell Leukaemia Viruses 1 to 4 (STLV1-4).

The deltaretroviruses encode an envelope of glycoprotein present in mature retrovirus viral particles. The envelope protein is synthesized in the form of a propeptide, which is cleaved in Golgi apparatus by furin peptidase, resulting in two polypeptides: the transmembrane (TM) and the cell surface (SU) components. The SU domain contains two major subdomains: a domain of interaction with the TM domain and the amino terminal RBD, the latest being liable to interact with host cell membrane receptors.

In one embodiment, the receptor-binding domain ligand is isolated from the envelope glycoprotein of Bovine Leukemia Virus, and is herein referred as BLV-RBD.

Consequently, in one embodiment, the ligand of the invention comprises the cell surface (SU) domain of the glycoprotein envelope of Bovine Leukemia Virus (BLV) or a fragment of the SU domain, such as, for example, the BLV-RBD. In another embodiment, the ligand of the invention does not comprise the transmembrane (TM) domain of the glycoprotein envelope of Bovine Leukemia Virus (BLV). Therefore, in one embodiment of the invention, the ligand of the invention is a soluble peptide, in particular a soluble BLV-RBD.

In one embodiment, the present invention thus relates to an in vitro or in vivo method for detecting and/or quantifying the cell surface nutrient transporter CAT1 present in a cell, wherein said method comprises:

a. contacting said cell with at least one bovine leukemia virus (BLV)-RBD ligand, a variant and/or a fragment thereof, and
b. determining and/or quantifying the binding of said at least one BLV-RBD ligand, variant or fragment thereof to CAT1.

In one embodiment, the method of the invention comprises a step of comparing the binding determined and/or quantified at step b. with a reference binding value.

In one aspect of the invention, the ligand is a BLV-RBD ligand, wherein said BLV-RBD ligand comprises a part or the totality of a receptor-binding domain (RBD) derived from the soluble part of a glycoprotein of the BLV enveloped virus that interacts with CAT1.

In one embodiment, said BLV-RBD comprises or consists of the amino acid sequence SEQ ID NO: 21 (encoded by SEQ ID NO: 22 or by SEQ ED NO: 5), variants or fragments thereof.

In one embodiment, said fragment comprises or consists of amino acids 34 to 181 of SEQ ID NO: 21.

In one embodiment, said fragment comprises or consists of amino acids 1 to 149, 150, 151, 152, 153, 154, 155, 156, 157, 158, 159, 160, 161, 162, 1.63, 164, 165, 166, 167, 168, 169, 170, 171, 172, 173, 174, 175, 176, 177, 178, 179, or 180 of SEQ ID NO: 21.

In another embodiment, said fragment comprises or consists of amino acids 34 to 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 of SEQ ID NO: 21.

In one embodiment, said BLV-RBD comprises or consists of the amino acid sequence SEQ ID NO: 28, variants or fragments thereof.

In one embodiment, said fragment comprises or consists of amino acids 34 to 181 of SEQ ID NO: 28.

In one embodiment, said fragment comprises or consists of amino acids 1 to 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 of SEQ ID NO: 28.

In another embodiment, said fragment comprises or consists of amino acids 34 to 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 of SEQ ID NO: 28.

In one embodiment, said BLV-RBD comprises or consists of the amino acid sequence SEQ ID NO: 29, variants or fragments thereof.

In one embodiment, said fragment comprises or consists of amino acids 34 to 181 of SEQ ID NO: 29.

In one embodiment, said fragment comprises or consists of amino acids 1 to 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 of SEQ ID NO: 29.

In another embodiment, said fragment comprises or consists of amino acids 34 to 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 of SEQ ID NO: 29.

In one embodiment, said BLV-RBD comprises or consists of the amino acid sequence SEQ ID NO: 4, variants or fragments thereof.

In one embodiment, said fragment comprises or consists of amino acids 34 to 181 of SEQ ID NO: 4.

In one embodiment, said fragment comprises or consists of amino acids 1 to 149, 150, 151, 152, 153, 154, 155, 156, 157, 158, 159, 160, 161, 162, 1.63, 164, 165, 166, 167, 168, 169, 170, 171, 172, 173, 174, 175, 176, 177, 178, 179, or 180 of SEQ ID NO: 4.

In another embodiment, said fragment comprises or consists of amino acids 34 to 149, 150, 151, 152, 153, 154, 155, 156, 157, 158, 159, 160, 161, 162, 163, 164, 165, 166, 167, 168, 169, 170, 1.71, 172, 173, 174, 175, 176, 177, 178, 179, or 180 of SEQ ID NO: 4.

In one embodiment, said BLV-RBD comprises or consists of the amino acid sequence SEQ ID NO: 3, variants or fragments thereof.

In one embodiment, said fragment comprises or consists of amino acids 34 to 215 of SEQ ID NO: 3.

In one embodiment, said fragment comprises or consists of amino acids 1 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 3.

In another embodiment, said fragment comprises or consists of amino acids 34 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 3.

In one embodiment, said BLV-RBD comprises or consists of the amino acid sequence SEQ ID NO: 30, variants or fragments thereof.

In one embodiment said fragment comprises or consists of amino acids 34 to 215 of SEQ ID NO: 30.

In one embodiment, said fragment comprises or consists of amino acids 1 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 30.

In another embodiment, said fragment comprises or consists of amino acids 34 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 30.

In one embodiment, said BLV-RBD comprises or consists of the amino acid sequence SEQ ID NO: 31, variants or fragments thereof.

In one embodiment, said fragment comprises or consists of amino acids 34 to 215 of SEQ ID NO: 31.

In one embodiment, said fragment comprises or consists of amino acids 1 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 31.

In another embodiment, said fragment comprises or consists of amino acids 34 to 182, 183, 184, 185, 186, 187, 188, 189, 190, 191, 192, 193, 194, 195,196, 197, 198, 199, 200, 201, 202, 203, 204, 205, 206, 207, 208, 209, 210, 211, 212, 213 or 214 of SEQ ID NO: 31.

In one embodiment, said BLV-RBD comprises or consists of the amino acid sequence SEQ ID NO: 32, variants or fragments thereof.

In one embodiment, said fragment comprises or consists of amino acids 34 to 215 of SEQ ID NO: 32.

In one embodiment, said fragment comprises or consists of amino acids 1 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 32.

In another embodiment, said fragment comprises or consists of amino acids 34 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213 or 214 of SEQ ID NO: 32.

In one embodiment, said BLV-RBD comprises or consists of the amino acid sequence SEQ ID NO: 13 (encoded by SEQ ID NO: 14), variants or fragments thereof.

In one embodiment, said BLV-RBD comprises or consists of the amino acid sequence SEQ ID NO: 15 (encoded by SEQ ID NO: 16), variants or fragments thereof.

In one embodiment, said BLV-RBD comprises or consists of the amino acid sequence SEQ ID NO: 17 (encoded by SEQ ID NO: 18), variants or fragments thereof.

In one embodiment, said BLV-RBD comprises or consists of the amino acid sequence SEQ ID NO: 19 (encoded by SEQ ID NO: 20), variants or fragments thereof.

In one embodiment, said BLV-RBD comprises or consists of the amino acid sequence SEQ ID NO: 33, variants or fragments thereof.

In one embodiment, said BLV-RBD comprises or consists of the amino acid sequence SEQ ID NO: 34, variants or fragments thereof.

In one embodiment, said BLV-RBD comprises or consists of the amino acid sequence SEQ ID NO: 35, variants or fragments thereof.

In one embodiment, said BLV-RBD comprises or consists of the amino acid sequence SEQ ID NO: 36, variants or fragments thereof.

In one embodiment, said BLV-RBD comprises or consists of the amino acid sequence SEQ ID NO: 37, variants or fragments thereof.

In one embodiment, said BLV-RBD comprises or consists of the amino acid sequence SEQ ID NO: 38, variants or fragments thereof.

In one embodiment, said BLV-RBD comprises or consists of the amino acid sequence SEQ ID NO: 39, variants or fragments thereof.

In one embodiment, said BLV-RBD comprises or consists of the amino acid sequence SEQ ID NO: 40, variants or fragments thereof.

In one embodiment, said BLV-RBD comprises or consists of the amino acid sequence SEQ ID NO: 41, variants or fragments thereof.

In one embodiment, said BLV-RBD comprises or consists of the amino acid sequence SEQ ID NO: 42, variants or fragments thereof.

In one embodiment, said BLV-RBD comprises or consists of the amino acid sequence SEQ ID NO: 43, variants or fragments thereof.

In one embodiment, said BLV-RBD comprises or consists of the amino acid sequence SEQ ID NO: 44, variants or fragments thereof.

In one embodiment, said BLV-RBD comprises or consists of the amino acid sequence SEQ ID NO: 45 (encoded by SEQ ID NO: 46), variants or fragments thereof.

In one embodiment, said BLV-RBD comprises or consists of the amino acid sequence SEQ ID NO: 47, variants or fragments thereof.

In one embodiment, said BLV-RBD comprises or consists of the amino acid sequence SEQ ID NO: 48, variants or fragments thereof.

In one embodiment, said BLV-RBD comprises or consists of the amino acid sequence SEQ ID NO: 49, variants or fragments thereof.

As used herein, "amino acids" are represented by their full name, their three letter code or their one letter code as well known in the art. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y: Histidine is His or H; Glutamine is Gin or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term "amino acids" includes both natural and synthetic amino acids, and both D and L amino acids. "Standard amino acid" or "naturally occurring amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. For example, naphtlylalanine can be substituted for tryptophan to facilitate synthesis. Other synthetic amino acids that can be substituted include, but are not limited to, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl.

As used herein, "amino acid" also encompasses chemically modified amino acids, including but not limited to, salts, amino acid derivatives (such as amides), and substitutions. Amino acids contained within the polypeptides of the present invention, and particularly at the carboxy- or amino-terminus, can be modified by methylation, amidation, acetylation or substitution with other chemical groups which can change the polypeptide's circulating half-life without adversely affecting their activity. Additionally, a disulfide linkage may be present or absent in the polypeptides of the invention.

The RBD ligands of the invention may comprise standard amino acids or non-standard amino acids. Polypeptide mimetics include polypeptides having the following modifications: i) polypeptides wherein one or more of the peptidyl —C(O)NR— linkages (bonds) have been replaced by a non-peptidyl linkage such as a —$CH_2$-carbamate linkage (—$CH_2OC(O)NR$—), a phosphonate linkage, a —$CH_2$-sulfonamide (—$CH_2$—$S(O)_2NR$—) linkage, a urea (—NHC(O)NH—) linkage, a —$CH_2$-secondary amine linkage, or with an alkylated peptidyl linkage (—C(O)NR—) wherein R is $C_1$-$C_4$ alkyl; ii) polypeptides wherein the N-terminus is derivatized to a —$NRR^1$ group, to a —NRC(O)R group, to a —NRC(O)OR group, to a —$NRS(O)_2R$ group, to a —NHC(O)NHR group where R and $R^1$ are hydrogen or $C_1$-$C_4$ alkyl with the proviso that R and $R^1$ are not both hydrogen; iii) polypeptides wherein the C terminus is derivatized to —$C(O)R^2$ where $R^2$ is selected from the group consisting of $C_1$-$C_4$ alkoxy, and —$NR^3R^4$ where Wand $R^4$ are independently selected from the group consisting of hydrogen and $C_1$-$C_4$ alkyl.

According to a preferred embodiment, the BLV-RBD ligands are selected from the group comprising the sequences SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 and 49, fragments and variants thereof, more preferably selected from the group comprising the sequences SEQ ID NO: 21 and 4, fragments and variants thereof, even more preferably selected from the group comprising the sequence SEQ ID NO: 21, fragments and variants thereof. According to another embodiment, receptor-binding domain ligands are encoded by a DNA sequence selected from the group comprising the sequence SEQ ID NO: 22, 5, 14, 16, 18, 20 and 46, variants and fragments thereof.

In one embodiment, the BLV-RBD ligand comprises or consists of a sequence presenting a sequence identity of at least 70% with one of the sequences SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49, preferably a sequence identity of at least about 75, 80, 85, 90, 91, 92, 93, 94, 95, 96, 97, 98, 99% or more with one of the sequences SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49.

In another embodiment, the BLV-RBD ligand of the invention is encoded by a DNA sequence presenting a sequence identity of at least 70% with the sequence SEQ ID NO: 22, 5, 14, 16, 18, 20 or 46, preferably a sequence identity of at least about 75, 80, 85, 90, 91, 92, 93, 94, 95, 96, 97, 98, 99% or more with the sequence SEQ ID NO: 22, 5, 14, 16, 18, 20 or 46.

In one embodiment, the BLV-RBD ligand of the invention is a variant of one of the polypeptide having the sequences SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 and 49.

A polypeptide "variant" as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences and evaluating one or more biological activities of the polypeptide as described herein and/or using any of a number of techniques well known in the art. Modifications may be made in the structure of polypeptides and still obtain a functional molecule that encodes a variant or derivative polypeptide with desirable characteristics.

When it is desired to alter the amino acid sequence of a polypeptide to create an equivalent, or even an improved, variant or portion of a ligand of the invention, one skilled in the art will typically change one or more of the codons of the encoding DNA sequence. For example, certain amino acids may be substituted by other amino acids in a protein structure without appreciable loss of its ability to bind cell surface receptor, preferably cell surface nutrient transporters. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences, or corresponding DNA sequences that encode said peptides without appreciable loss of their biological utility or activity. In many instances, a polypeptide variant will contain one or more conservative substitutions. A "conservative substitution" is one in which an amino acid is substituted by another amino acid that has similar properties, such that one skilled in the art of peptide chemistry would expect the secondary structure and hydropathic nature of the polypeptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include histidine, lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) Ala, Pro, Gly, Glu, Asp, Gin, Asn, Ser. Thr; (2) Cys, Ser, Tyr, Thr; (3) Val, Ile, Leu, Met, Ala, Phe; (4) Lys, Arg, His; and (5) Phe, Tyr, Trp, His.

As used herein, the term "conservative amino acid substitution" may further be defined as an amino acid exchange within one of the following five groups:

I. Small aliphatic, nonpolar or slightly polar residues: Ala, Ser, Thr, Pro, Gly, II. Polar, negatively charged residues and their amides: Asp, Mn, Glu, Gln, III. Polar, positively charged residues: His, Arg, Lys,
IV. Large, aliphatic, nonpolar residues: Met, Leu, lie, Val, Cys,
V. Large, aromatic residues: Phe, Tyr, Trp.

A variant may also, or alternatively, contain non-conservative changes. In a preferred embodiment, variant polypeptides differ from a native sequence by substitution, deletion or addition of 1.2, 3, 4, 5, 6, 7, 8, 9 or 10 amino acids. Variants may also (or alternatively) be modified by, for example, the deletion or addition of amino acids that have minimal influence on the immunogenicity, secondary structure and hydropathic nature of the polypeptide.

In one embodiment, a variant of SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49 is capable of binding to CAT1 with an affinity at least equivalent to the one of SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49 respectively.

In one embodiment, a variant of SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49 comprises conservative amino acid substitutions as compared to the sequence of SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49, respectively, such as, for example, 1, 2, 3, 4, 5, 6, 7, 8, 9 or 10 conservative amino acid substitutions.

In another embodiment, a variant of SEQ ID NO: 21, 3, 4, 13, 15, 17, 19, 28, 29, 30, 31, 32, 33, 34, 35, 36, 37, 38, 39, 40, 41, 42, 43, 44, 45, 47.48 or 49 is a polypeptide wherein 1, 2, 3, 4, 5, 6, 7, 8, 9 or 10 amino acids from the sequence of SEQ ID NO: 21, 3, 4, 13, 15, 17, 19, 28, 29, 30, 31, 32, 33, 34, 35, 36, 37, 38, 39, 40, 41, 42, 43, 44, 45, 47, 48 or 49, respectively, is/are absent, or substituted by any amino acid, or wherein 1, 2, 3, 4, 5, 6, 7, 8, 9 or 10 amino acids (either contiguous or not) is are added.

In one embodiment of the invention, the RBD ligands as described here above are modified by means well-known in the art, for instance by the addition of one or more functional group such as a phosphate, acetate, lipid or carbohydrate group, and/or by the addition of one or more protecting group. For example, the RBD ligands can be modified by the addition of one or more functional groups such as phosphate, acetate, or various lipids and carbohydrates. The RBD ligands of the invention can also exist as polypeptide derivatives. The term "polypeptide derivative" refers to compound having an amino group (—NH—), and more particularly, a peptide bond. Polypeptides may be regarded as substituted amides. Like the amide group, the peptide bond shows a high degree of resonance stabilization. The C—N single bond in the peptide linkage has typically about 40 percent double-bond character and the C═O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosyl, benzyl and dinitrophenyl. The indole group of tryptophan may be protected by formyl or may not be protected.

The modification of the RBI) ligands aims in particular to improve their life time in vivo. One type of modification is the addition to the N- or C-termini of the RBD ligands of polyethylene glycol (PEG). PEG is known by the person skilled in the art to have many properties that make it an ideal carrier for polypeptides such as high water solubility, high mobility in solution and low immunogenicity. This modification also protects the polypeptides from exopeptidases and therefore increases their overall stability in vivo.

The other modifications used to prevent degradation of the polypeptides by endopeptidases or exopeptidases include N-terminal modifications such as acetylation or glycosylation, C-terminal modifications such as amidation and use of unnatural amino acids (n-amino and α-trifluoromethyl amino acids) at particular sites within the polypeptides. In one embodiment, the BLV-RBD ligand of the invention is glycosylated. In another embodiment, the BLV-RBD ligand of the invention is not glycosylated.

Another alternative to increase polypeptide molecular size is the genetic fusion of the polypeptides to the Fc domain of human immunoglobulin (including, for example, IgA, IgM and IgG) or the fusion of the polypeptides to albumin.

In one embodiment; the BLV-RBD ligand as described here above is a fusion protein comprising a part or the totality of a RBD fused to a detection tag, such as, for example, a Fc fragment or a GFP. Examples of Fc fragments include, but are not limited to, rabbit Fc fragment (amino acid sequence SEQ ID NO: 8, encoded by SEQ ID NO: 9), mouse Fc fragment (amino acid sequence SEQ ID NO: 10, encoded by SEQ ID NO: 11).

In one embodiment, the receptor-binding domain ligand is BLV-RBD fused to rabbit Fc fragment (that may be encoded, for example, by the DNA sequence SEQ ID NO: 12).

In one embodiment, the receptor-binding ligand of the invention is coupled with at least one contrast agent. Non-limiting examples of contrast agents are listed hereinabove. A preferred contrast agent is I-125.

The RBD ligands of the invention described herein can be produced synthetically by chemical synthesis or enzymatic synthesis as it is well known in the art. Alternatively, nucleotide sequences encoding the polypeptides of the invention can be introduced into a protein expression vector and produced in a suitable host organism (e.g., bacteria, insect cells, etc.), then purified. In one embodiment, the receptor-binding domain ligand is obtained by a cloning method, such as, for example, using any production system known in the art, such as, for example, *E. coli*, yeast, baculovirus-insect cell, or mammalian cells such as HEK or CHO, expression system.

Another object of the invention is a BLV-RBD ligand as described hereinabove coupled with at least one contrast agent. In one embodiment, the at least one contrast agent is a radiolabeled agent or a fluorescent agent. In one embodiment, the at least one contrast agent is I-125.

In one embodiment, the at least one BLV-RBD ligand coupled with at least one contrast agent may be used as a probe for medical imaging.

Methods for coupling at least one contrast agent to a RBD ligand are well known in the state of the art. For instance, the at least one contrast agent may be bound covalently or non-covalently.

For example, technics to couple polypeptides to 1-125 are well known in the state of the art. A non-limited example of such a method is the following: iodine present in a reduced form (NaI) reacts with the phenol group of a tyrosine or with the side chain of a histidine residue. These groups are pre-oxidized with an oxidizing agent (iodogen). The peptides preparation (100 μg for 1 mci=37 MBq) is then added to an iodogen solution and incubated for 10 minutes at 4° C. The reaction is stopped using a stop solution comprising for example 200 μL of PBS with sodium azide per marking. In parallel, a mouse serum is added onto a PD10 column. Then the reaction solution is added onto the PD10 column and the peptide coupled with the iodine is collected.

In one embodiment of the invention, the at least one BLV-RBD ligand, variant and/or fragment thereof coupled with at least one contrast agent of the invention is for use as a tracer. The term "tracer", as used herein, refers to a recognition agent providing insight into CAT1-related disease location, progression and/or structure for pre-, intra- and post-operative surgery.

The present invention thus further relates to an in vivo method for tracing cells infected or not yet infected by BLV or wherein the function of a cationic L-amino acid transporter, preferably the CAT1 function, is dysregulated, in a subject in need thereof, comprising:

a. administering an effective amount of at least one BLV-RBD ligand, a variant and/or a fragment thereof coupled with at least one contrast agent to the subject, and b. detecting and/or quantifying said at the least one BLV-RBD ligand, variant and/or fragment thereof binding to said cells using medical imaging technics.

In one embodiment, said method is for use in pre-, intra-, or post-operative surgery. In another embodiment, said method is for use in fluorescence guided surgery.

Examples of specific medical imaging technics methods that may be used are well known to the skilled artisan and include, but are not limited to, for instance computer assisted tomography (CAT), magnetic resonance spectroscopy (MRS), magnetic resonance imaging (MRI), positron emission tomography (PET) or single-photon emission computed tomography (SPECT) and are described in Boonstra et al. (2015. Oncotarget 6(16): 14260-73).

In one embodiment, the BLV-RBD ligand as described above is coupled with a radiolabeled agent or a fluorescent agent as described herein. Examples of radiolabeled agent or fluorescent agent that may be used for targeting include, but are not limited to, I-125, I-131, F-18 (i.e. 18-F-fluoro-2-deoxy-D-glucose, 18-F-fluoro-17-estradiol), 11-C-acetate, Tc-99m O-15, N-13, Br-76, In-111, Cu-64, Ga-68, Zr-89, ZW800-1, Cy5.5, IRDye800CW.

The term "cationic L-amino acid transporter-related disease, preferably CAT1-related disease" as used herein refers to diseases wherein pathways involving arginine, lysine, ornithine or histidine homeostasis and/or metabolism are dysregulated.

Examples of cationic L-amino acid transporter-related diseases, preferably of CAT1-related diseases, include, but are not limited to, arginine-related diseases, lysine-related diseases, histidine-related diseases, ornithine-related diseases, nitric oxide-related diseases, and inflammatory diseases.

Examples of arginine-related diseases include, but are not limited to, arginine-related cancers, argininosuccinate lyase-related diseases, argininosuccinate synthetase-related diseases, cardiac fibrosis and muscle fibrosis.

Examples of arginine-related cancers include, but are not limited to, arginine-related tumors, arginine-related sarcomas, arginine-related leukemia, arginine-related carcinomas, arginine-related lymphoma, arginine-related metastasis, and arginine-related melanomas, argininosuccinate synthetase-related cancers, argininosuccinate lyase related cancers, arginine auxotroph tumors and acute myeloid leukemia.

Examples of argininosuccinate synthetase-related cancers include, but are not limited to, colorectal cancer, bladder cancer, pancreatic cancer, liver cancer, melanoma, nasopharyngeal carcinoma, hepatocellular carcinoma, myxofibrosarcoma, brain tumor, glioblastoma, uveal melanoma, lung carcinoma, small cell lung cancer, colon carcinoma, colorectal cancer, hepatic carcinoma, renal cell carcinoma, prostate cancer, breast cancer, non-Hodgkin's lymphoma, Hodgkin's lymphoma, pancreatic carcinoma, malignant melanoma, osteosarcoma, malignant pleural mesothelioma, esophageal adenocarcinoma, pulmonary metastasis, ovarian cancer, acute myelocystic leukemia, mesothelial cancer, urological cancer and Burkitt lymphoma.

Examples of argininosuccinate lyase-related diseases include, but are not limited to, liver cancer, liver fibrosis, colorectal cancer, argininosuccinate lyase deficiency, argininosuccinic aciduria, urea cycle disorders, hyperammonemia, developmental retardation, acute infection or stress to cognitive impairment, behavioral abnormalities, and/or learning disabilities, hepatomegaly, progressive encephalopathy, lethargy, seizures, attention deficit hyperactivity disorder, hepatitis, cirrhosis, systemic hypertension, hypokalemia and glioblastoma.

Examples of argininosuccinate synthetase-related diseases include, but are not limited to, citrullinemia I, hyperammonemia, urea cycle disorders, and argininosuccinate synthetase related cancers.

Examples of lysine-related diseases include, but are not limited to, hyperlysinemia, glutaric aciduria type I, L-2 hydroxyglutaric aciduria, D-2 hydroxyglutaric aciduria, and herpes simplex infection.

Examples of histidine-related diseases include, but are not limited to, histidinemia, and histidine ammonia-lyase deficiency.

Examples of ornithine-related diseases include, but are not limited to, ornithine transcarbamylase deficiency, cirrhosis, and carcinogenesis.

Examples of nitric oxide-related diseases include, but are not limited to, chronic renal failure, chronic heart failure, congestive heart failure, hypertension, atherosclerosis, stroke, and thrombosis.

Examples of metabolic diseases include, but are not limited to, obesity, diabetes, cardiovascular mortality, renal damage and ischemia.

Examples of inflammatory diseases include, but are not limited to, polyarthritis, rheumatoid arthritis, asthma, inflammatory bowel diseases, celiac diseases, autoimmune diseases and multiple sclerosis.

Bovine leukemia virus infects dairy and bovine or ovine cattle's blood cells and mammary tissue. The retrovirus is easily transmitted among cattle primarily through direct contact, infected blood, milk and possibly by biting insects. In addition, recent studies demonstrated an increased risk for women exposed to BLV to develop breast cancer.

Examples of BLV infection include, but are not limited to, leukemia, persistent lymphocytosis, lymphoproliferation, lymphoid tumors, malignant B cell lymphoma, Enzootic bovine leucosis (in cows) and breast cancer.

In one embodiment, the method of the invention is for diagnosing a cationic L-amino acid transporter-related disease, preferably a CAT1-related disease, or a BLV infection. In one embodiment, the method of the invention is not for diagnosing an inflammatory state.

The present application thus relates to a method for the diagnosis of a cationic L-amino acid transporter-related disease, preferably a CAT1-related disease, or a BLV infection comprising the steps of:

a. contacting an effective amount of at least one BLV-RBD ligand, a variant and/or a fragment thereof to a cell, sample, tissue, and/or organ,
b. detecting and/or quantifying the binding of the at least one BLV-RBD ligand, variant and/or fragment thereof to CAT1 in said cell, sample, tissue, and/or organ.

In one embodiment, the method of the invention comprises a step of comparing the binding determined and/or quantified at step b. with a reference binding value.

As used herein, the term "reference" broadly encompasses any suitable reference binding level which may be used as a basis for comparison with respect to the determined binding. In one embodiment, the reference is constructed using algorithms and/or other methods of statistical and hierarchical classification. In another aspect, the reference binding level is stored in a database to provide a stored binding level and the stored binding level is used to determine the difference in the binding level. The database may, for example, be stored on a computer or a server.

In one embodiment, the reference binding level is an index value or is derived from one or more risk prediction algorithms or computed indices for the presence of cells wherein the function of a cationic L-amino acid transporter, preferably the CAT1 function, is dysregulated or cells infected or not yet infected by BLV. A reference binding level can be relative to a number or value derived from population studies, including without limitation, such populations of subjects having similar age range, subjects in the same or similar ethnic group.

The term "cells wherein a cationic L-amino acid transporter, preferably the CAT1 function is dysregulated" as used herein refers to cells wherein arginine or lysine or histidine or ornithine metabolism or influx is abnormally increased or decreased.

Arginine or lysine or histidine or ornithine metabolisms include their synthesis, catabolism but also dietary uptake. Arginine is synthetized by two key enzymes: argininosuccinate synthetase and argininosuccinate lyase, that exhibit deficient or abnormal activities in diverse pathologies which results in arginine accumulation in some organs, tissues, samples, or cells affected or not yet affected by these pathologies. Lysine and histidine are essential amino acids, and are therefore not synthesized in animals. Omithine is involved in the production of urea via the action of enzyme arginase on L-arginine.

In one embodiment of the invention, the reference binding level is the binding level measured in a population of patients diagnosed with a cationic L-amino acid transporter-related disease, preferably a CAT1-related disease, or a BLV infection.

According to this embodiment, equivalence (i.e., an absence of difference) between the determined binding level and the reference binding level, or a determined binding level superior to the reference binding level may be indicative of the presence of a cationic L-amino acid transporter-related disease, preferably a CAT1-related disease, or an infection with BLV.

In one embodiment of the invention, the reference binding level is the binding level determined in a population of substantially healthy subjects, i.e., in a population of subjects not diagnosed with a cationic L-amino acid transporter-related disease, preferably a CAT1-related disease, or a BLV infection. According to this embodiment, a determined binding level superior to the reference binding level may be indicative of the presence of a cationic L-amino acid transporter-related disease, preferably of a CAT1-related disease, or a BLV infection.

In the present invention, two numeric values, in particular two binding levels, are considered as different if the first numeric value is higher (such as, for example, the first numeric value is about 20% higher than the second one, preferably is about 30, 40, 50, 60, 70, 80, 90% or more higher than the second one) or lower than the second one (such as, for example, the second numeric value is about 20% lower than the second one, preferably is about 30, 40, 50, 60, 70, 80, 90% or more lower than the second one).

In one embodiment, the reference value is a personalized reference, determined earlier in the same subject (such as, for example, before receiving a treatment for a cationic L-amino acid transporter-related disease, preferably a CAT1-related disease, or a BIN infection).

In one embodiment, the at least one BLV-RBD ligand, variant and/or fragment thereof is a BLV-RBD ligand coupled with at least one contrast agent as described hereinabove.

In one embodiment, the diagnosis method of the invention is an in vivo diagnosis method. Preferably, said diagnosis method is based on medical imaging.

In another embodiment, the diagnosis method of the invention is an in vitro or ex vivo method, i.e., the method of the invention is performed on a cell, sample, tissue and/or organ that was obtained from a patient prior to the implementation of the method of the invention. Consequently, in one embodiment, the method of the invention does not comprise obtaining a sample from the patient, i.e., the method of the invention is non-invasive.

In one embodiment, the method of the invention is for monitoring a cationic L-amino acid transporter-related disease, preferably a CAT1-related disease, in a subject. In one embodiment, the method of the invention is for monitoring a BLV infection in a subject. The term "monitoring" as used herein refers to the determination of the amount of cells wherein arginine, lysine, histidine or ornithine metabolism is dysregulated in the body of a subject as a function of time, such as, for example, before, during and after a therapy against a cationic L-amino acid transporter-related disease, preferably against a CAT1-related disease, or against a BLV infection.

The term "therapy against a cationic L-amino acid transporter-related disease, preferably against a CAT1-related disease or against a BLV infection" as used herein may refer to arginine deprivation, chemotherapy, radiation, surgery, immunotherapy, and drugs known to the skilled artisan as drugs for treating a cationic L-amino acid transporter-disease (including a CAT1-related disease) or a BLV infection.

In one embodiment, the method of monitoring of the invention comprises comparing two binding levels, such as, for example, a binding determined before treatment with a binding level determined after treatment.

In one embodiment, a decreased binding level of the at least one BLV-RBD ligand after treatment is indicative of the efficacy of the treatment.

In one embodiment, a binding level after treatment equivalent or superior to the one determined before treatment is indicative of the absence of efficacy of the treatment.

The present application also relates to a method for monitoring a cationic L-amino acid transporter-related disease, preferably a CAT1-related disease, or a BLV infection in a subject comprising the steps of:

a. contacting an effective amount of at least one BLV-RBD ligand, a variant and/or a fragment thereof, preferably coupled with at least one contrast agent, to a cell, sample, tissue, and/or organ of said subject,
b. detecting and/or quantifying the binding of the at least one BLV-RBD ligand, variant and/or fragment thereof to CAT1 in said cell, sample, tissue, and/or organ, preferably by medical imaging,
c. treating the subject with a therapy against a cationic L-amino acid transporter-related disease, preferably against a CAT1-related disease, or against a BLV infection,
d. contacting an effective amount of the at least one BLV-RBD ligand, variant and/or fragment thereof, preferably coupled with at least one contrast agent to a cell, sample, tissue, and/or organ of said subject, and
e. detecting and/or quantifying the binding of the at least one BLV-RBD ligand, variant and/or fragment thereof to CAT1 in said cell, sample, tissue, and/or organ.

In one embodiment, the method of the invention further comprises a step of comparing the binding determined in step e) with the binding determined in step b), thereby monitoring a cationic L-amino acid transporter-related disease, preferably a CAT1-related disease, or a BLV infection in the subject.

In one embodiment, the absence or the decrease of detection of CAT1 in a cell, sample, tissue, and/or organ after a therapy against a cationic L-amino acid transporter-related disease (including a CAT1-related disease), or against a BIN infection, is indicative of a remission. In particular, such disease may include for example nitric oxide-related diseases, preferably chronic renal failure and chronic heart failure.

In another embodiment, the presence or the increase of detection of CAT1 in a cell, sample, tissue, and/or organ after a therapy against a cationic L-amino acid transporter-related disease (including a CAT1-related disease) is indicative of a remission. In particular, such disease may include metabolic diseases such as for example, obesity, diabetes, cardiovascular mortality, renal damage or ischemia.

The present application further relates to a composition comprising, consisting or consisting essentially of at least one BLV-RBD ligand, a variant and/or a fragment thereof as described hereinabove.

The present application further relates to a pharmaceutical composition comprising, consisting or consisting essentially of at least one BLV-RBD ligand, a variant and/or a fragment thereof as described hereinabove and at least one pharmaceutically acceptable excipient.

The present application further relates to a medicament comprising, consisting or consisting essentially of at least one BLV-RBD ligand, a variant and/or a fragment thereof as described hereinabove.

As used herein, the term "consisting essentially of" with reference to a pharmaceutical composition or medicament, means that the at least one BLV-RBD ligand of the invention is the only one therapeutic agent or agent with a biologic activity within said pharmaceutical composition or medicament.

The present application also relates to a diagnostic composition comprising, consisting or consisting essentially of at least one BLV-RBD ligand, a variant and/or a fragment thereof coupled with at least one contrast agent as described hereinabove and at least one pharmaceutically acceptable excipient.

In one embodiment, the diagnostic composition of the invention is for diagnosing a cationic L-amino acid transporter-related disease, preferably a CAT1-related disease or for monitoring a cationic L-amino acid transporter-related disease, preferably a CAT1-related disease, according to the methods of the invention as described hereinabove. In another embodiment, the diagnostic composition of the invention is for diagnosing a BLV infection or for monitoring a BLV infection, according to the methods of the invention as described hereinabove. In one embodiment, the diagnostic composition of the invention is not for diagnosing an inflammatory state.

Pharmaceutically acceptable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene- polyoxypropylene-block polymers, polyethylene glycol and wool fat.

In addition, pharmaceutically acceptable excipients may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfate, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

The present application also relates to at least one BLV-RBD ligand, composition, pharmaceutical composition or medicament as described hereinabove for treating or for use in treating a cationic L-amino acid transporter-related disease, preferably a CAT1-related disease, or a BLV infection.

In one embodiment, the at least one BLV-RBD ligand, composition, pharmaceutical composition or medicament as described hereinabove is not for treating or for use in treating an inflammatory state.

In one embodiment, the at least one BLV-RBD ligand, composition, pharmaceutical composition or medicament as described hereinabove is not a vaccine. Thus, in one embodiment, the at least one BLV-RBD ligand, composition, pharmaceutical composition or medicament as described hereinabove is not for generating or for use in generating antibodies, in particular, antibodies directed against BLV.

The present application also relates to a method for treating a cationic. L-amino acid transporter-related disease, preferably a CAT1-related disease, or a BLV infection, wherein the method comprises administering to the subject a therapeutically effective amount of at least one BLV-RBI) ligand as described here above.

The present application also relates to a method for targeting cells, samples, tissues, and/or organs infected or not yet infected by BLV or wherein the function of a cationic L-amino acid transporter, preferably the CAT1 function is dysregulated, wherein said method comprises administering at least one BLV-RBD ligand, a variant and/or a fragment thereof to a subject. Such method may be used, for example, for targeting therapeutic agents to cells, samples, tissues, and/or organs infected or not yet infected by BLV or wherein the function of a cationic L-amino acid transporter, preferably the CAT1 function is dysregulated. In one embodiment, the methods of the invention are for protecting a subject from other subjects already infected by BLV, or for preventing a BLV infection and in particular for preventing the propagation of a BLV infection.

In one embodiment, said at least one BLV-RBD ligand, preferably when coupled with at least one contrast agent, is encapsulated. The encapsulation of the at least one BLV-RBD ligand coupled with at least one contrast agent may avoid any degradation. The technics of encapsulation are well known in the state of the art.

Examples of capsule include, but are not limited to, phospholipids, polymers, liposomes and quantum dots.

In one embodiment, the at least one BLV-RBD ligand is encapsulated with a therapeutic agent to be specifically administered to cells, samples, tissues or organs infected or not yet infected by BLV or wherein the function of a cationic L-amino acid transporter, preferably of CAT1 function is dysregulated within the subject's body.

In one embodiment, the at least one BLV-RBD ligand, the at least one BLV-RBD ligand coupled with at least one contrast agent, the composition, the diagnostic composition, the pharmaceutical composition or the medicament of the invention is to be administered at a dose determined by the skilled artisan and personally adapted to each subject.

In one embodiment, the at least one BLV-RBD ligand, the at least one BLV-RBD ligand coupled with at least one contrast agent, the composition, the diagnostic composition, the pharmaceutical composition or the medicament of the invention is to be administered at an effective amount.

It will be understood that the usage of the at least one BLV-RBD ligand, the at least one BLV-RBD ligand coupled with at least one contrast agent, the composition, the diagnostic composition, the pharmaceutical composition or the medicament of the invention will be decided by the attending physician within the scope of sound medical judgment. The specific effective amount for any particular patient will depend upon a variety of factors including the specific composition employed, the age, body weight, general health, sex and diet of the subject; the time of administration, route of administration, and like factors well known in the medical arts.

In one embodiment, the at least one BLV-RBD ligand, the at least one BLV-RBD ligand coupled with at least one contrast agent, the composition, the diagnostic composition, the pharmaceutical composition or the medicament of the invention is to be administered by injection, orally, topically, nasally, buccally, rectally, vaginally, intratracheally, by endoscopy, transmucosally, or by percutaneous administration.

In one embodiment, the at least one BLV-RBD ligand, the at least one BLV-RBI) ligand coupled with at least one contrast agent, the composition, the diagnostic composition, the pharmaceutical composition or the medicament of the invention is to be administered by injection, preferably is to be systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal, intravitreal, and intraperitoneal injection, or perfusion. In another embodiment, when injected, the composition, the diagnostic composition, the pharmaceutical composition or the medicament of the invention is sterile. Methods for obtaining a sterile composition, diagnostic composition, pharmaceutical composition or medicament include, but are not limited to, GMP synthesis (GMP stands for "Good manufacturing practice").

In one embodiment, the at least one BLV-RBD ligand, the at least one BLV-RBD ligand coupled with at least one contrast agent, the composition, the diagnostic composition, the pharmaceutical composition or the medicament of the invention is to be orally administered. Examples of formulations adapted to oral administration include, but are not limited to, solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid forms adapted to oral administration include, but are not limited to, solutions, suspensions, drinkable solutions, elixirs, sealed phial, potion, drench, syrup and liquor.

In another embodiment, the at least one BLV-RBD ligand, the at least one BLV-RBD ligand coupled with at least one contrast agent, the composition, the diagnostic composition, the pharmaceutical composition or the medicament of the invention is to be topically administered. Examples of formulations adapted to topical administration include, but are not limited to, sticks, waxes, creams, lotions, ointments, balms, gels, masks, leave-on washes and/or the like.

Depending on the cell(s), sample(s), tissue(s) and/or organ(s) targeted, the skilled artisan can determine the technology needed for the introduction of the at least one BLV-RBD ligand in the targeted cell(s), sample(s), tissue(s) and/or organ(s).

In one embodiment, the at least one BLV-RBD ligand, the at least one BLV-RBD ligand coupled with at least one contrast agent, the composition, the diagnostic composition, the pharmaceutical composition or the medicament of the invention is to be administered in a sustained-release form. In another embodiment, the at least one BLV-RBD ligand, the at least one BLV-RBD ligand coupled with at least one contrast agent, the composition, the diagnostic composition, the pharmaceutical composition or the medicament of the invention comprises a delivery system that controls the release of the agent.

The "targeted cell(s), sample(s), tissue(s) and/or organ(s)" as used herein may refer to (a) cell(s), (a) sample(s), (a) tissue(s) and/or (an) organ(s) affected or suspected to be affected by a cationic L-amino acid transporter-related disease, preferably by a CAT1-related disease, or by a BIN infection.

In one embodiment, a therapeutically effective amount of the BLV-RBD ligand, the BLV-RBD ligand coupled with at least one contrast agent, the pharmaceutical composition or medicament of the invention is administered at least once a day, twice a day, or at least three times a day.

In another embodiment, a therapeutically effective amount of the BLV-RBD ligand, the BLV-RBD ligand coupled with at least one contrast agent, the pharmaceutical composition or medicament of the invention is administered every two, three, four, five, or six days.

In another embodiment, a therapeutically effective amount of the BLV-RBD ligand, the BIN-RBD ligand coupled with at least one contrast agent, the pharmaceutical composition or medicament of the invention is administered every week, twice a week, every two weeks, or once a month.

In another embodiment, a therapeutically effective amount of the at least one BLV-RBD ligand, the at least one BLV-RBD ligand coupled with at least one contrast agent, the pharmaceutical composition or the medicament of the invention is administered every month for a period at least 2; 3; 4; 5; or 6 months.

In another embodiment, a therapeutically effective amount of the at least one BLV-RBD ligand, the at least one BLV-RBD ligand coupled with at least one contrast agent, the pharmaceutical composition or the medicament of the invention ranges from about 1 μg to 5 g.

In another embodiment, a therapeutically effective amount of the at least one BLV-RBD ligand, the at least one BLV-RBD ligand coupled with at least one contrast agent, the pharmaceutical composition or the medicament of the invention is to be administered ranges from about 0.1 μg/kg to 1 g/kg.

In another embodiment, the at least one BLV-RBD ligand, the at least one BLV-RBD ligand coupled with at least one contrast agent, the composition, the pharmaceutical composition or the medicament of the invention as described here above is to be administered in combination with another treatment for a cationic L-amino acid transporter-related disease, preferably for a CAT1-related disease, or for a BIN infection.

Examples of agents for treating a cationic L-amino acid transporter-related diseases, preferably CAT1-related diseases, or BLV infections include, but are not limited to, arginine deprivation, chemotherapy, radiation, surgery, protein kinases inhibitors, microtubules inhibitors, anti-metabolite agents a tumor vaccine or an immunostimulatory antibody.

In one embodiment of the invention, the method for treating a cationic L-amino acid transporter-related disease, preferably a CAT1-related disease, or a BLV infection in a subject in need thereof, comprises administering to the subject the at least one BLV-RBD ligand, the at least one BLV-RBD ligand coupled with at least one contrast agent, the composition, the pharmaceutical composition or the medicament of the invention prior to, concurrent to and/or posterior to another treatment against a cationic L-amino acid transporter-related disease, preferably against a CAT1-related disease, or against a BIN infection.

In one embodiment, the subject is affected, preferably is diagnosed with a cationic L-amino acid transporter-related disease, preferably with a CAT1-related disease, or with a BLV infection. In another embodiment, the subject of the invention is at risk of developing a cationic L-amino acid transporter-related disease, preferably a CAT1-related disease, or a BLV infection. Examples of risk factor for developing a cationic L-amino acid transporter-related disease, preferably a CAT1-related disease, include, but are not limited to, genetic factors, smoking, obesity, diabetes, alcohol, and environmental conditions. Examples of risk factor for developing a BIN infection, include, but are not limited to, environmental conditions such as, for example, exposure to other subjects infected by BLV.

In another embodiment, the subject of the invention is in a remission stage following a cationic L-amino acid transporter-related disease, preferably following a CAT1-related disease.

Another object of the present invention is a kit for implementing the method of the invention, wherein said kit comprises means for detecting and/or quantifying CAT1 in a cell, sample, tissue and/or organ, and in particular for determining the binding of the at least one BLV-RBD ligand to CAT1.

In one embodiment, the kit of the invention comprises at least one BLV-RBD ligand coupled with at least one contrast agent as described here above.

By "kit" is intended any manufacture (e.g., a package or a container) comprising at least one reagent (such as, for example, a BLV-RBD ligand coupled with at least one contrast agent) for specifically detecting and/or quantifying CAT1. The kit may be promoted, distributed, or sold as a unit for performing the methods of the present invention. Furthermore, any or all of the kit reagents may be provided within containers that protect them from the external environment, such as in sealed and sterile containers. The kits may also contain a package insert describing the kit and methods for its use.

Another object of the present invention is a screening method for detecting and/or quantifying compounds modulating CAT1 function in a cell comprising:

a. determining and/or quantifying the binding of a BLV-RBD ligand as described hereinabove to CAT1 expressed in a cell in the presence of said compound, and
b. comparing the binding measured at the previous step with a binding of a BLV-RBD ligand as described hereinabove to CAT1 expressed in said cell in the absence of said compound.

The terms "modulating" and "modulation" as used herein may thus refer to an increase or decrease of the presence of CAT1 in a cell.

The present application also relates to a method for the in vitro or ex vivo or in vivo diagnosis of a cationic L-amino acid transporter-related disease, preferably of a CAT1-related disease, or a BLV infection comprising:

a. contacting at least one BLV-RBD ligand, a variant and/or a fragment thereof with a cell, a sample, a tissue or an organ, and
b. detecting and/or quantifying the at least one BLV-RBD ligand bound to CAT1 present in the cell, sample, tissue or organ within said subject.

The present application also relates to a method for the in vivo diagnosis of a cationic L-amino acid transporter-related disease, preferably of a CAT1-related disease, or a BLV infection comprising:

a. administering to a subject in need thereof an effective amount of at least one BLV-RBD ligand, a variant and/or a fragment thereof, and
b. detecting and/or quantifying the at least one BLV-RBD ligand, variant and/or fragment thereof within said subject.

In one embodiment, of the invention, the BLV-RBD ligand is coupled with at least one contrast agent, and may be used for in vivo diagnosis by medical imaging.

The present application also relates to a method for treating a cationic L-amino acid transporter-related disease, preferably a CAT1-related disease, or a BLV infection comprising:

a. diagnosing a cationic L-amino acid transporter-related disease, preferably a CAT1-related disease, or a BLV infection in a subject in need thereof according to the method of the invention, and
b. administering a therapeutically effective amount of a therapy against a cationic L-amino acid transporter-related disease, preferably a CAT1-related disease, or against a BLV infection to said subject diagnosed in step (a) with a cationic L-amino acid transporter-related disease, preferably with a CAT1-related disease, or with a BIN infection.

In one embodiment, the method for treating a cationic L-amino acid transporter-related disease, preferably a CAT1-related disease, or a BLV infection of the invention thus comprises:

a. determining the presence of cells wherein the function of a cationic L-amino acid transporter, preferably the CAT1 function, is dysregulated, or of cells infected by BLV (or not yet infected by BLV), in a subject in need thereof by:
   i. administering an effective amount of at least one BLV-RBD ligand, a variant and/or a fragment thereof coupled with at least one contrast agent to a subject, and
   ii. detecting and/or quantifying the at least one BLV-RBD ligand, variant and/or fragment thereof using medical imaging, and
b. administering a therapeutically effective amount of a therapy against a cationic L-amino acid transporter-related disease, preferably against a CAT1-related disease, or against a BLV infection, to a subject diagnosed in step a. with a cationic L-amino acid transporter-related disease, preferably with a CAT1-related disease, or with a BLV infection.

The present application also relates to a method for treating a cationic L-amino acid transporter-related disease, preferably a CAT1-related disease, or a BLV infection comprising administering a therapeutically effective amount of at least one BLV-RBD, a variant and/or a fragment thereof to a subject in need thereof.

The present application also relates to a method for treating a cationic L-amino acid transporter-related disease, preferably a CAT1-related disease, or a BLV infection comprising:

a. diagnosing a cationic L-amino acid transporter-related disease, preferably a CAT1-related disease, or a BLV infection in a subject in need thereof according to the method of the invention, and
b. administering a therapeutically effective amount of at least one BLV-RBD, a variant and/or a fragment thereof to said subject diagnosed in step a. with a cationic L-amino acid transporter-related disease, preferably with a CAT1-related disease, or with a BLV infection.

The present application also relates to an in vivo method for detecting and/or quantifying CAT1 in a cell comprising:

a. administering at least one BIN-RBD ligand, a variant and/or a fragment thereof coupled with at least one contrast agent or the diagnostic composition of the invention to a body, an organ, a tissue or a cell,
b. detecting and/or quantifying the binding of the at least one BLV-RBD ligand, variant and/or fragment thereof binding to CAT1 in said body, organ, tissue or cell using medical imaging technics.

In one embodiment, the method of the invention further comprises comparing the binding determined in step b. with a reference binding.

The present application also relates to a method for inhibiting CAT1 activity in a subject in need thereof wherein a therapeutically effective amount of at least one BLV-RBD ligand is administered to said subject.

The term "inhibiting CAT1 activity" as used herein may refer to an inhibition of the flux of arginine, histidine, lysine and/or ornithine transport within a cell by CAT1.

Examples

Figure 1:
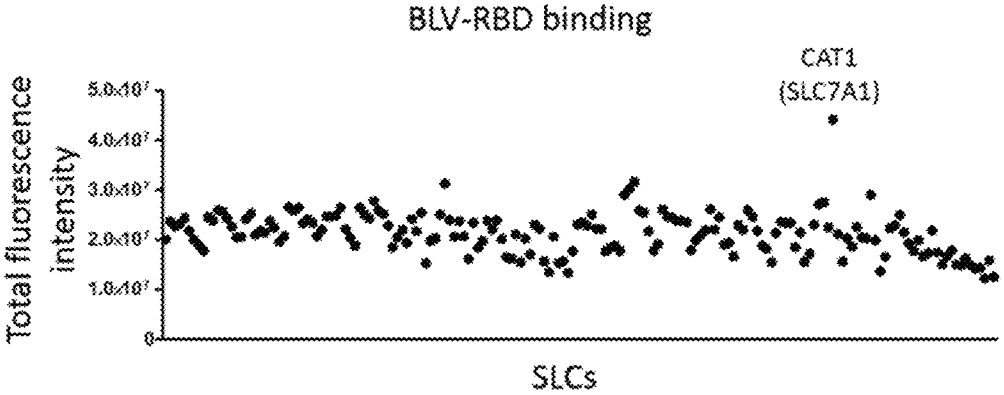
FIG. 1 is a graph showing the BLV-RBD automated screen identifying CAT1 as the BLV-RBD cognate receptor. Screening for BLV-RBD binding on the 172 SLC members was performed with the Tecan robot and Cellomics microscope. Binding is expressed as total fluorescence intensity for each well.

The present invention will now be further illustrated by, but is by no means limited to, the following examples.

Example 1: Specific Binding of BLV-RBD to CAT1

Materials and Methods

Cell Culture and Transfection

All cell lines were maintained in DMEM culture medium (Dulbecco's Modified Eagle Medium) supplied by Life Technologies (ref: 11965-092) with 10% decomplemented fetal bovine serum (PAN Biotech); non-essential amino acids (11140-035, Life Technologies): glutamine (25030-081 Life Technologies) and antibiotics (penicillin and streptomycin). All were incubated at 37° C. in a 5% CO2-95% air atmosphere.

20 000 QTC cells were seeded in a 96-well plate. Cells were transfected with 100 ng of DNA using. JetPrime transfection protocol. Conditions for binding with BLV-RBD were optimized for automated conditions.

Staining for Team Robot and Cellomics Microscope

Staining was performed 48 hours post-transfection, using a BLV-RBD-mFc ligand (SEQ ID NO: 27). For this purpose, RBD ligands were tested at a 1/10 (v:v) dilution and the anti-mouse IgG1 bound to Alexa Fluor® 488 was used (1 to 500 dilutions).

Incubation of the RBD ligand is performed at 37° C. without shaking and the secondary anti-mouse IgG1-Alexa is incubated at room temperature (as opposed to 4° C. in previous protocol). Cells were then fixed with 4% PFA and fluorescence intensity was measured using the Cellomics Array Scan XTI HCS reader (Thermo Scientific; available at the CNRS MRI platform).

The SLC candidate detected by the high-throughput screening was confirmed by both siRNA and overexpression in HEK293T cells (data not shown).

Because of the natural expression of the BLV receptor on 293T cells and the looser attachment of HEK293T cell monolayers to plastic, we choose to use quail QT6 cells, which had lowest natural binding of our BLV-RBD ligands and a monolayer attachment to plastic compatible with the automated screening of our SLC library. We chose to set up the Cellomics-based fluorescent automated assay that would allow the detection and quantification potentially isolated foci off the quail QT6 cell monolayer that would be highly fluorescent from expression of the BLV-RBD cognate receptor.

Results

A SLC library containing 172 of the nearly 400 described members, coming from the human ORFeome (MGC platform) completed with constructs that were derived in our laboratory was established. We proceeded to set up an automated protocol of transient overexpression in the quail QT6 cell line and binding with a BLV-RBD tagged in frame with the constant fragment of the mouse immunoglobulin (mFc), in order to detect and isolate the BLV receptor.

Accordingly, when HEK293T cells are transfected with siRNA specifically designed to target CAT1 mRNA, BLV-RBD binding has a 3.5-fold decrease as measured by flow cytometry (n=3). In contrast, when HEK293T cells are transfected with CAT1/SLC7A1 expression vector, CAT1 overexpression in these cells is accompanied by a 3-time-increase of BLV-RBD binding when compared to HEK293T cells transfected with an empty vector control (n=3).

Figure 2:
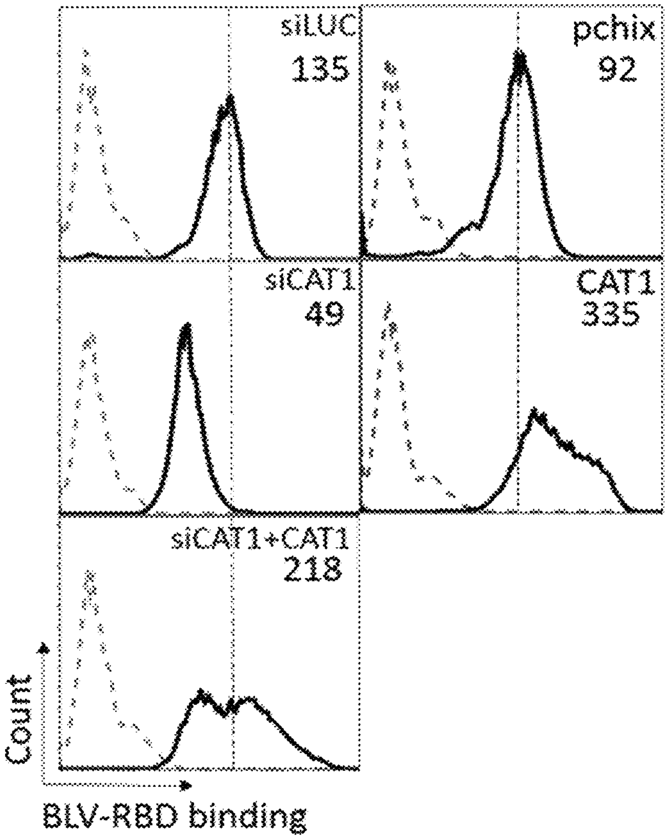
FIG. 2 is a set of graphs showing the specific BLV-RBD binding to CAT1/SLC7A1. HEK293T cells were transfected with either of siLUC, siCAT1, siCAT1 combined with CAT1 expression vector (rescue assay), empty vector (pchix) or CAT1 expression vector only. CAT1 expression level was monitored using BLV-RBD ligand.

Our screening method provides evidence for CAT1 (SLC7A1) as the BLV-RBD and BLV Env receptor (FIG. 1). From the results as seen in FIG. 1, we focused our attention on CAT1 (SLC7A1) as the putative receptor for BLV-RBD ligand. Accordingly, down modulation of CAT1 mRNA by specific siRNA (siCAT1 5'-UAAUUGCACC-UUUGGCUGCTT-3'— SEQ ID NO: 6) resulted in a highly significant decrease of the binding with BLV-RBD on. HEK293T cells (135 vs 49, FIG. 2). We performed a rescue assay (co-transfection of siCAT1 and CAT1 expression plasmid) and were able to restore CAT1 expression as monitored with BLV-RBD ligand (49 vs 218, FIG. 2). Moreover, BLV-RBD can be used to monitor specific increase expression of CAT1 when comparing cells either transfected with the pCH1X control empty vector or a human CAT1 expression vector (92 vs 335, FIG. 2).

Example 2: BLV-RBD-Induced Inhibition of Arginine Uptake in Cells

Materials and Methods

Uptake Assays $3.5\times10^5$ HEK293T cells per well were seeded in a 6-well plate coated with poly-D The following day, the cells were transfected using calcium phosphate with the vectors: pCSI rabbit Fc (rFc), pCSI BLV-RBD rFc (SEQ ID NO: 12) et pCSI HTLV2.RBD rFc (SEQ ID NO: 7). 16 hours post-transfection, the cell medium was changed and 24 hours later, the cells were seeded in 24-well plates ($5\times10^4$ cells/well) for the uptake of L-arginine or L-glutamine radiolabeled or in 6-well plates ($3\times10^5$ cells/well) to lyse the cells and verify the expression of RBD by immunoblotting.

For uptake, cells were incubated in a volume of 250 μL for 30 minutes at 37° C. with 5 μCi/mL of L-arginine monohydrochloride [2,3,4-$^3$H] (NET1123250UC, Perkin Elmer) or L-glutamine [3,4-$^3$H (N)] (NET551001MC Perkin Elmer) diluted in DMEM classic. After two washes with cold PBS, cells were lysed with 500 μL Triton X-100 1% and mixed with 2 mL of liquid scintillation cocktail (ULTIMA GOLD, Perkin Elmer) before measuring the radioactivity.

The values of the assimilation correspond to the ratio between the captured quantity (pmol) of arginine or glutamine radiolabeled and the amount (mg) of proteins in each well. The results were calculated and are reported using GraphPad Prism 5. The bilateral statistical test for unpaired data Student was used.

Results

The ability of BLV-RBD to functionally alter its cognate receptor upon binding was tested. For this purpose, uptake assays were performed and it allowed us to monitor whether BLV-RBD tagged with mouse Fc (mFc) (data not shown) or rabbit Fc (rFc) can block the transporter function using radiolabeled arginine.

CAT1 is described to be ubiquitously expressed in all cell types except in liver and lacrimal gland and to mediate sodium-independent transport of cationic L-amino acids that include arginine, lysine, ornithine and histidine.

Figure 3:
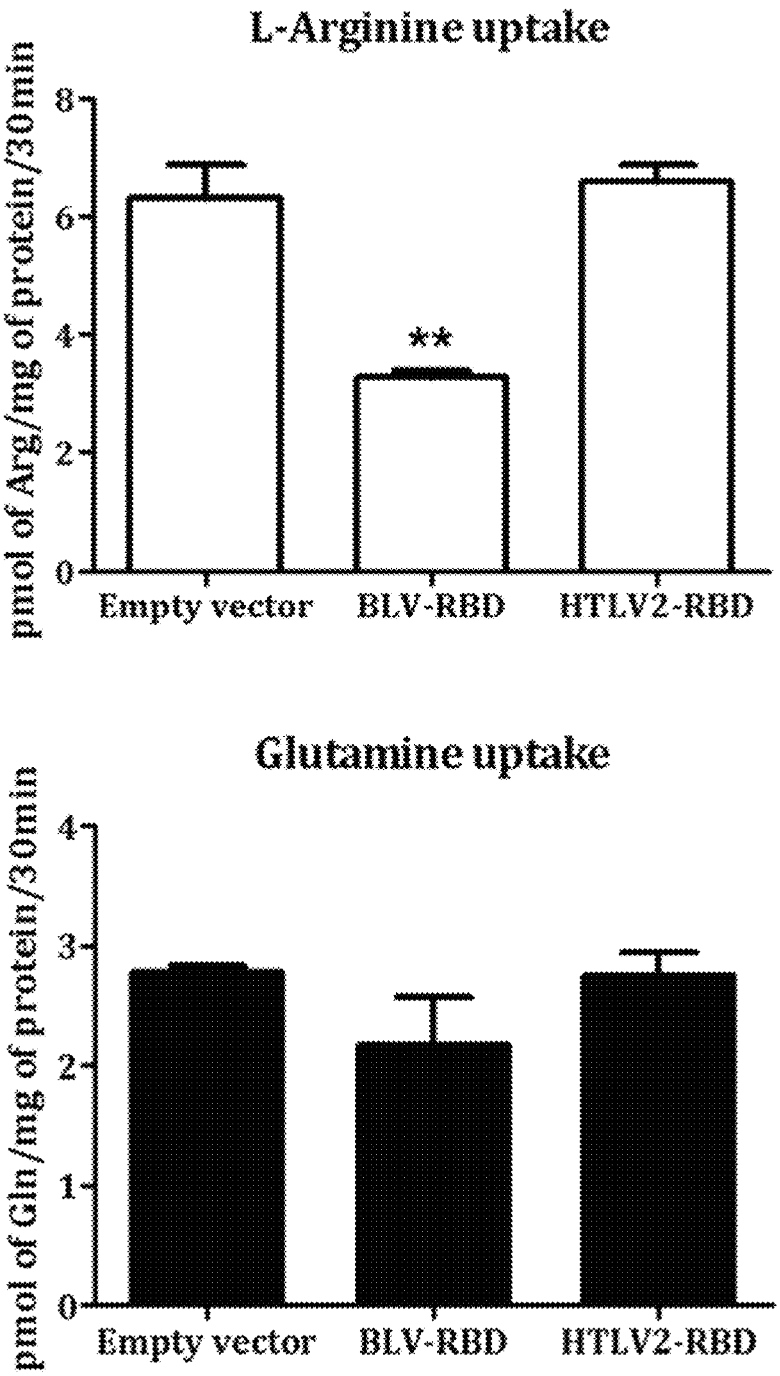
FIG. 3 is a set of 2 histograms showing the specific inhibition of arginine uptake by the receptor-binding domain of the bovine leukemia virus envelope glycoprotein (BLV-RBD). Uptake of radiolabeled arginine and glutamine by HEK293T cells transfected with either of: pCSImFc empty vector ("empty vector"). BLV-RBD fused to a rFc tag in pCSI expression vector ("BLV-RBD", SEQ ID NO: 12), or HTLV2.RBD fused to a rFc tag in pCSI expression vector ("HTLV2-RBD", SEQ ID NO: 7). N-3, bilateral Student test on unpaired data (**, $p<0.01$; all other differences are not statistically significant).

Using radiolabeled arginine monohydrochloride. L-[2,3,4-$^3$H] provides further evidence of BLV-RBD binding of CAT1/SLC7A1. Thus, arginine transport, which is mediated by CAT1, is inhibited upon introduction of BLV-RBD and data show that BLV-RBD can block CAT1 transport function (FIG. 3).

These results demonstrate that BLV-RBD ligand can be used to monitor CAT1 cell-surface expression and can be applied in a large variety of biological samples. BLV-RBD ligand can therefore be used in vitro by flow cytometry, immunohistochemistry (not shown) and immunofluorescence or in vivo by SPECT-CT imaging.

Example 3: Test In Vitro of the Effect of BIN-RBD on a BIN Infection

Materials and Methods

Materials

Infection of A23 cell line stably expressing CAT1 from different mammal species (A23-LXSN: empty vector; A23-CAT1human; A23-Cat1 cattle; A23-mouse Cat1 mouse and A23-hamster Cat1).

Culture medium: HEK293 cells are grown up in DMEM with 10% FBS, L-glutamine, nonessential amino acids and antibiotics (Penicillin streptomycin). The producing cells (HEK293) and the infected A2.3 cells will encode for GFP.

Method

At Day 0 (D0): seed 4 Petri dishes (10 cm diameter) with HEK293 cells (ATCC) $3\times10^6$ cells/dish.

At D1 (evening): transfection of HEK293 in order to produce viral pseudotypes coding for the following envelopes (HTLV2; BLV; Vesicular stomatitis Indiana virus (VSV) or without envelope). Co-transfection with the following vectors:

LNCG (code for GFP): 10 μg,

BEB.GP57 (gag-poi): 5 μg,

Envelope glycoprotein: 5 μg.

Calcium phosphate transfection (500 μL of HeBS and 33 μL of CaCl2).

At D2 (morning): change the medium of the HEK293 cells.

At D3: collect and filter the supernatant of HEK293 cells (to keep for infection with the supernatant); detach and count the producing cells (for cell to cell infection).

Infection with the Supernatant

Seed the A23 cells (LXSN; hCAT1; bovineCAT1; mouseCAT1 and hamsterCAT1): 5000 cells/well in a 96-well plate (make sure to have 5000 cells in 50 μL of medium). Add an equal volume (50 μL) of the viral supernatant. N=4.

Cell to Cell Infection

Co-culture of the different indicator cells (A23) with the producing cells (HEK293). Seed 2500 cells/well of A23 with 2500 cells of pseudotype producing cells for each condition (e.g. A23-LXSN with HEK293 producing pseudotypes). N=4.

At D5: (only for cell to cell infection). Add the selection agent (2 mg/mL of G418). In this way, we will eliminate the producer cells which are sensitive, while A23 are resistant.

D8: image (10×) and fluorescence intensity acquiring with High Content Cellomics ArrayScan (available at Montpellier Rio Imaging Platform: MRI).

Example 4: Test In Vitro of the Retroviral Infection by a BIN Env Glycoprotein Harboring a BLV-RBD, Via CAT1 Binding Viral Infection CHO cells stably transfected with the empty pLXSN expression vector or with a pLXSN construct expressing either human (Hu-) or bovine (B-) CAT1, or the human CAT2 isoform were plated in 6-well plates and infected the following day with serial dilutions of replication-defective pLKO-1-puro lentiviral vector pseudotyped with the BLV or HTLV Env glycoproteins. One day after viral challenge, cells were selected with 3 ug/mL puromycin during 10 days and resistant cells were counted to determine viral titers due to entry using the BLV or HTLV Env.

Results

Figure 4:
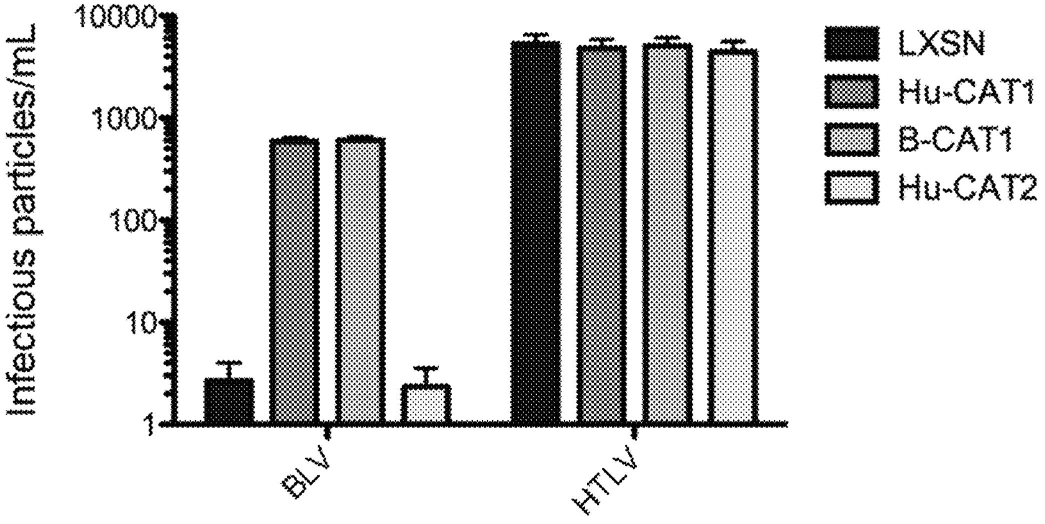
FIG. 4 is an histogram showing infectivity trials, using CHO cells. Infectiveness of BLV (left panel) and HTLV (right panel) were tested, in cells transfected with an empty pLXSN expression vector as negative control (LXSN), or a pLXSN vector expressing human CAT1 (Hu-CAT1), bovine CAT1 (B-CAT1) or human CAT2 (Hu-CAT2). Results are shown as the number of infectious particles/mL.

CHO cells susceptibility to HTLV Env-mediated infection is independent of CAT1 or CAT2 expression (FIG. 4, right panel); in contrast. CHO cells, which are naturally resistant to BLV Env-mediated infection (FIG. 4, left panel, black histogram), become specifically susceptible to BIN Env-mediated infection when expressing either human (FIG. 4, left panel, dark grey histogram) or bovine (FIG. 4, left panel, grey histogram) CAT1, while remaining resistant upon expression of the human CAT2 isoform (FIG. 4, left panel, light grey histogram).

These results confirm that the bovine leukemia virus (BIN) envelope glycoprotein binds specifically to CAT1 of different mammals, including cattle and humans, but not to CAT2.

The invention claimed is:

1. A method for detecting and/or quantifying the cationic amino acid transporter-1 (CAT1) in a cell, wherein said method comprises:
   (a) contacting said cell with one and only one ligand comprising a bovine leukemia virus-RBD ligand (BLV-RBD ligand), a variant and/or a fragment thereof, and
   (b) determining and/or quantifying the binding of said BLV-RBD ligand, a variant and/or fragment thereof to CAT1 by detecting and/or quantifying a complex formed between CAT1 and said BLV-RBD ligand, variant or fragment thereof,
   wherein said BLV-RBD ligand comprises the sequence of SEQ ID NO: 21, a variant and/or fragment thereof,
   wherein said variant of a BLV-RBD ligand comprises a sequence presenting a sequence identity of at least 85% with SEQ ID NO: 21 and
   wherein said fragment of a BLV-RBD ligand comprises or consists of amino acids 34 to 149 of SEQ ID NO: 21.

2. The method according to claim 1, wherein said method further comprises comparing the binding level determined and/or quantified at step (b) with a reference value.

3. A method for diagnosing or monitoring a CAT1-related disease in a subject, wherein said method comprises:
   (a) contacting a cell with one and only one ligand comprising a bovine leukemia virus-RBD ligand (BLV-RBD ligand), a variant and/or a fragment thereof,
   (b) determining and/or quantifying the binding of said BLV-RBD ligand, variant and/or fragment thereof to CAT1 by detecting and/or quantifying a complex formed between CAT1 and said BLV-RBD ligand, variant or fragment thereof,
   (c) comparing the binding level determined and/or quantified at step (b) with a reference binding value, wherein an equivalence or a binding level greater than the reference binding level is indicative of the presence of a CAT1-related disease,
   wherein said BLV-RBD ligand comprises the sequence of SEQ ID NO: 21, a variant and/or fragment thereof,
   wherein said variant of a BLV-RBD ligand comprises a sequence presenting a sequence identity of at least 85% with SEQ ID NO: 21,
   wherein said fragment of a BLV-RBD ligand comprises or consists of amino acids 34 to 149 of SEQ ID NO: 21, and
   wherein said CAT1-related disease is selected from arginine-related cancers, argininosuccinate lyase-related diseases, argininosuccinate synthetase-related cancers or diseases, cardiac fibrosis, muscle fibrosis, hyperlysinemia, glutaric aciduria type I, L-2 hydroxyglutaric aciduria, D-2 hydroxyglutaric aciduria, herpes simplex infection, histidinemia, histidine ammonia-lyase deficiency, ornithine transcarbamylase deficiency, cirrhosis, carcinogenesis, chronic renal failure, chronic heart failure, congestive heart failure, hypertension, atherosclerosis, stroke, thrombosis, polyarthritis, rheumatoid arthritis, asthma, inflammatory bowel diseases, celiac diseases, autoimmune diseases, multiple sclerosis, obesity, diabetes, cardiovascular mortality, renal damage and ischemia.

4. The method according to claim 1, being an in vitro method.

5. The method according to claim 3, being an in vivo method, wherein the method comprises administering to a subject in need thereof the BLV-RBD ligand, a variant and/or a fragment thereof.

6. The method according to claim 5, being an in vivo method for diagnosing or monitoring a CAT1-related disease in a subject by medical imaging, wherein the ligand is coupled with at least one contrast agent.

7. The method according to claim 1, wherein said variant of the BLV-RBD ligand comprises a sequence selected from the list consisting of SEQ ID NO: 4, 28 and 29.

8. The method according to claim 3, being an in vitro method.

9. The method according to claim 3, wherein said variant of the BLV-RBD ligand comprises a sequence selected from the list consisting of SEQ ID NO: 4, 28 and 29.

* * * * *